(12) United States Patent
Navarro et al.

(10) Patent No.: US 8,545,906 B2
(45) Date of Patent: Oct. 1, 2013

(54) PEST-IMPERVIOUS PACKAGING MATERIAL AND PEST-CONTROL COMPOSITION

(75) Inventors: Shlomo Navarro, Holon (IL); Simcha Finkelman, Shoham (IL); Dov Zehavi, Rehovot (IL); Refael Dias, Hadera (IL); Sam Angel, Rishon LeZion (IL); Fadel Mansur, Usfiya (IL); Miriam Rindner, RaAnana (IL)

(73) Assignees: The State of Israel, Ministry of Agriculture & Rural Development, Agricultural Research Organization (ARO) (Volcani Center), Beit-Dagan (IL); Biopack Ltd., Caesarea (IL)

( * ) Notice: Subject to any disclaimer, the term of this patent is extended or adjusted under 35 U.S.C. 154(b) by 172 days.

(21) Appl. No.: 12/790,891

(22) Filed: May 31, 2010

(65) Prior Publication Data

US 2010/0236971 A1   Sep. 23, 2010

Related U.S. Application Data

(63) Continuation of application No. 10/816,861, filed on Apr. 5, 2004.

(30) Foreign Application Priority Data

Mar. 18, 2004   (IL) .......................................... 160950

(51) Int. Cl.
*A01N 65/00*   (2009.01)
(52) U.S. Cl.
USPC ........... 424/756; 424/405; 424/406; 424/407; 424/408; 424/409; 514/729; 514/730; 514/731; 514/732; 514/733; 514/734
(58) Field of Classification Search
None
See application file for complete search history.

(56) References Cited

U.S. PATENT DOCUMENTS

| | | | |
|---|---|---|---|
| 2,001,478 | A | 5/1935 | Vogt |
| 3,044,885 | A | 7/1962 | Loehr |
| 3,156,661 | A | 11/1964 | Feinberg |
| 3,493,464 | A | 2/1970 | Bowers et al. |
| 3,653,873 | A | 4/1972 | Bayer |
| 3,728,213 | A | 4/1973 | Hinz |
| 3,864,468 | A | 2/1975 | Hyman et al. |
| 3,959,556 | A | 5/1976 | Morrison |
| 3,998,944 | A | 12/1976 | Long |
| 4,008,351 | A | 2/1977 | Inoue et al. |
| 4,111,922 | A | 9/1978 | Beede et al. |

(Continued)

FOREIGN PATENT DOCUMENTS

| | | |
|---|---|---|
| EP | 0026897 | 7/1984 |
| EP | 0726074 | 8/1996 |

(Continued)

OTHER PUBLICATIONS

K. Jayaprakasha, et al in A.Naturforschung 56c 40-44 (2001) Chemical Composition of Turmeric Oil.*

Golding et al. "Structures of α- and β-Turmerone", Journal of the Chemical Society Perkin Transactions, 1: 1519-1524, 1992.

Golob et al. "The Use of Spices and Medicinals as Bioactive Protectants for Grains", FAO Agricultural Services Bulletin, Food and Agriculture Organization of the United Nations Rome, 137(Chap.2, 3h, 6): 7 P., 1999.

(Continued)

*Primary Examiner* — Neil Levy

(57) ABSTRACT

A composition-of-matter comprising a substance usable in producing packaging material and at least one compound selected from the group consisting of ar-turmerone, a sesquiterpene alcohol and a turmeric oleoresin solid residue.

7 Claims, 4 Drawing Sheets

(56) References Cited

U.S. PATENT DOCUMENTS

| | | | |
|---|---|---|---|
| 4,160,335 | A | 7/1979 | Von Kohorn et al. |
| 4,214,909 | A | 7/1980 | Mawatari et al. |
| 4,343,853 | A | 8/1982 | Morrison |
| 4,401,712 | A | 8/1983 | Morrison |
| 4,533,435 | A | 8/1985 | Intili |
| 4,581,227 | A * | 4/1986 | Kjelleberg et al. ............. 424/49 |
| 4,663,077 | A | 5/1987 | Rei et al. |
| 4,666,706 | A | 5/1987 | Farquharson et al. |
| 4,743,448 | A | 5/1988 | Bahadir et al. |
| 4,818,525 | A | 4/1989 | Kamada et al. |
| 4,842,875 | A | 6/1989 | Anderson |
| 4,879,078 | A | 11/1989 | Antoon, Jr. |
| 4,888,175 | A | 12/1989 | Burton, Jr. et al. |
| 4,910,032 | A | 3/1990 | Antoon, Jr. |
| 4,923,650 | A | 5/1990 | Antoon, Jr. et al. |
| 4,990,381 | A | 2/1991 | Holzner |
| 4,997,650 | A | 3/1991 | Kamada et al. |
| 5,011,698 | A | 4/1991 | Antoon, Jr. et al. |
| 5,023,247 | A | 6/1991 | Boulanger et al. |
| 5,045,331 | A | 9/1991 | Antoon, Jr. |
| 5,160,768 | A | 11/1992 | Antoon, Jr. |
| 5,242,052 | A | 9/1993 | Weder |
| 5,254,401 | A | 10/1993 | Kelch et al. |
| 5,256,377 | A * | 10/1993 | Nakamaru et al. ............. 422/122 |
| 5,688,509 | A | 11/1997 | Radwan et al. |
| 5,843,215 | A | 12/1998 | Whalon et al. |
| 5,985,010 | A | 11/1999 | Etscorn et al. |
| 6,190,710 | B1 | 2/2001 | Nir et al. |
| 6,534,078 | B1 | 3/2003 | Strzemiemski et al. |
| 6,914,077 | B2 * | 7/2005 | Nagatsuka et al. ........... 514/557 |
| 7,396,546 | B2 * | 7/2008 | Rosenbloom ................ 424/729 |
| 2005/0208157 | A1 | 9/2005 | Navarro et al. |

FOREIGN PATENT DOCUMENTS

| | | |
|---|---|---|
| EP | 1245152 | 10/2002 |
| FR | 2697133 | 4/1994 |
| JP | 49-006920 | 2/1974 |
| JP | 05-070388 | 3/1993 |
| JP | 07-112907 | 5/1995 |
| JP | 08-081306 | 3/1996 |
| JP | 200328611 | 10/2003 |
| WO | WO 94/05151 | 3/1994 |
| WO | WO 97/29638 | 8/1997 |
| WO | WO 00/00022 | 1/2000 |
| WO | WO 2005/087003 | 9/2005 |

OTHER PUBLICATIONS

Martins et al. "Essential Oil Composition and Antimicrobial Activity of Three Zingiberaceae From S. Tomé e Príncipe", Planta Medicine, 67: 580-584, 2001.
Communication Pursuant to Article 94(3) EPC Dated Dec. 27, 2007 From the European Patent Office Re.: Application No. 04101309.5.
Communication Pursuant to Article 94(3) EPC Dated Aug. 31, 2009 From the European Patent Office Re.: Application No. 04101309.5.
Communication Pursuant to Article 96(2) EPC Dated Jun. 26, 2006 From the European Patent Office Re.: Application No. 04101309.5.
European Search Report Dated Jun. 21, 2005 From the European Patent Office Re.: Application No. 04101309.5.
International Preliminary Report on Patentability Dated Sep. 28, 2006 From the International Bureau of WIPO Re.: Application No. PCT/IL2004/000284.
Invitation Pursuant to Article 94(3) and Rule 71(1) EPC Dated Apr. 20, 2009 From the European Patent Office Re.: Application No. 04101309.5.
Notice of Allowance Dated Feb. 22, 2010 From the US Patent and Trademark Office Re.: U.S. Appl. No. 10/816,861.
Office Action Dated May 27, 2007 From the Israeli Patent Office Re.: Application No. 160950.
Official Action Dated May 2, 2008 From the US Patent and Trademark Office Re.: U.S. Appl. No. 10/816,861.
Official Action Dated Feb. 4, 2009 From the US Patent and Trademark Office Re.: U.S. Appl. No. 10/816,861.
Official Action Dated Dec. 6, 2007 From the US Patent and Trademark Office Re.: U.S. Appl. No. 10/816,861.
Official Action Dated Sep. 24, 2009 From the US Patent and Trademark Office Re.: U.S. Appl. No. 10/816,861.
Response Dated Jan. 25, 2010 to Official Action of Sep. 24, 2009 From the US Patent and Trademark Office Re.: U.S. Appl. No. 10/816,861.
Response Dated Dec. 30, 2009 to Communication Pursuant to Article 94(3) EPC of Aug. 31, 2009 From the European Patent Office Re.: Application No. 04101309.5.
Summons to Attend Oral Proceedings Pursuant to Rule 115(1) EPC Dated Nov. 4, 2008 From the European Patent Office Re.: Application No. 04101309.5.
Antony "Chemistry, Technology and Uses in Food Industry—A Review", Kancor Technical Forum, http://www.kancorflavours.com/html/k0431bis.htm, 2 P., 2001.
Aratanechemuge et al. "Selective Induction of Apoptosis by Ar-Turmerone Isolated From Turmeric (*Curcuma longa* L) in Two Human Leukemia Cell Lines, But Not in Human Stomach Cancer Cell Line", International Journal of Molecular Medicine, 9: 481-484, 2002.
He et al. "Liquid Chromatography-Electrospray Mass Spectrometric Analysis of Curcuminoids and Sesquiterpenoids in Turmeric (*Curcuma longa*)", Journal of Chromatography A, 818: 127-132, 1998.
Jilani et al. "Repellent and Feeding Deterrent Effects of Turmeric Oil, Sweetflag Oil, Neem Oil, and A Neem-Based Insecticide Against Lesser Grain Borer (Coleoptera: Bostrychidae)", Journal of Economic Entomology, 83(2): 629-634, 1990.
Leal et al. "Functional Properties of Spice Extracts Obtained Via Supercritical Fluid Extraction", Journal of Agriculture and Food Chemistry, 51: 2520-2525, 2003.
Lee et al. "Insecticidal Activities of Ar-Turmerone Identified in *Curcuma longa* Rhizome Against *Nilaparvata lugens* (Homoptera: Delphacidae) and *Plutella Xylostella* (Lepidoptera: Yponomeutidae)", Journal of Asia Pacific Entomology, 4(2): 181-185, 2001. Abstract.
Ohshiro et al. "Structures of Sesquiterpenes From *Curcuma longa*", Phytochemistry, 29(7): 2201-2205, 1990.
Raina et al. "Essential Oil Composition of *Curcuma longa* L. Cv. Roma From the Plants of Northern India", Flavour and Fragrance Journal, 17(2): 99-102, 2002. Abstract.
Raina et al. "Turning to Turmeric", www.essentiallyoils.com/Newsletter/May_2000_News.../may_2000_newsletter.htm, Newsletter, 2000. Abstract.
Sharma et al. "Essential Oils of *Curcuma longa* L. From Bhutan", Journal of Essential Oil Research, 9(5): 589-592, 1997. Abstract.
Singh et al. "Chemical Composition and Biological Activity of Essential Oil of *Pogostemon plectranthoides* Desf.", Indian Perfumer, 45(1): 35-38, 2001, Chemical Abstracts, HCAPLUS ACS on STN, DN: 136:366392.
Su et al. "Isolation, Purification, and Characterization of Insect Repellents From *Curcuma longa* L.", Journal of Agriculture and Food Chemistry, 30: 290-292, 1982. p. 291, col. 1, § 6—col. 2, § 4, p. 292, col. 1, §5—col. 2, § 1.
Yatagai et al. "Extractives From Yakusugi Bogwood and Their Termicitidal Activity and Growth Regulation Effects on Plant Seeds", Mokuzai Gakkaishi, 37(4): 345-351, 1991. Chemical Abstracts, HCAPLUS ACS on STN, DN: 115:106318.
Zwavig et al. "Analysis of the Essential Oils of Five *Curcuma* Species", Flavour and Fragrance Journal, 7(1): 19-22, 1992. Abstract.
Decision to Grant a European Patent Pursuant to Article 97(1) EPC Dated Sep. 9, 2010 From the European Patent Office Re.: Application No. 04101309.5.
Office Action Dated Jan. 7, 2013 From the Israel Patent Office Re. Application No. 192509 and Its Translation Into English.

* cited by examiner

First fractionation of 12B:

Second fractionation of 12B:

ar-Turmerone (5): Mr=216

PEST-IMPERVIOUS PACKAGING MATERIAL AND PEST-CONTROL COMPOSITION

RELATED APPLICATION/S

This application is a continuation of U.S. patent application Ser. No. 10/816,861 filed Apr. 5, 2004, which claims the benefit of priority of Israel Patent Application No. 160950 filed Mar. 18, 2004.

The contents of all of the above applications are incorporated by reference as if fully set forth herein.

FIELD AND BACKGROUND OF THE INVENTION

The present invention relates to a packaging material which includes turmeric compounds such as ar-turmerone, sesquiterpene alcohols and/or turmeric oleoresin solid residue and thus is resistant to pest infestation, and a pest control composition which includes sesquiterpene alcohols and/or turmeric oleoresin solid residue, and methods of production and use thereof.

Packaged products such as foodstuffs contained in a conventional packaging material are susceptible to infestation by as many 500 species of insects and mites, which are capable of perforating the packaging material or which use existing holes or openings in the food packaging for penetration. Presently, under prevailing stringent standards of sanitation, any level of pest infestation of stored foodstuff is considered unacceptable. To prevent such infestation, it would be highly desirable to render the packaging material impervious to pest penetration as opposed to treating the food items directly with potentially hazardous pesticides.

U.S. Pat. Nos. 3,156,661; 4,818,525; 4,990,381; 4,997,650; and 5,023,247 describe coating compositions of synthetic pesticides which can be used in a packaging material. However, such pesticides can be toxic to humans and thus are gradually being restricted from agricultural or domestic use. Accordingly, any use of synthetic pesticides in packaged goods in general, and in packaged foodstuff in particular, is substantially restricted by regulation. As a consequence, the search for naturally-occurring and safe pest control agents which can be used to prevent pest infestation of packaged goods effectively and safely has become increasingly important.

Naturally-occurring and nontoxic pest control agents may be isolated from plants as many plants inherently produce various compounds that protect them from pests, and which may affect the behavior of a wide range of pest species. Accordingly, leaves, roots, twigs and flowers of certain plant species have been used to protect stored food items from pests in different parts of the world, particularly India, China and Africa.

One of the plant species which has been recognized for its pest control attributes (as well as for its special medicinal and nutritional attributes) is Turmeric (*Curcuma longa* L.). It is a tropical plant of the Zingiberaceae family indigenous to southern Asia, known to contain pungent odoriferous oils, oleoresins and other related compounds. The turmeric oleoresins consist of curcuminoids, essential oil and other related compounds.

Jilani and Su (1983) reported that petroleum ether turmeric extract repelled *Tribolium castaneum* (the red flour beetle), four weeks after application. They also found that the chief components of turmeric oil are sesquiterpene ketones in the form of turmerone and ar-turmerone.

Pranata (1984) reported that petroleum ether turmeric extract was acutely toxic to *C. maculatus*.

Jilani et al. (1988) reported that turmeric oil repelled *T. castaneum* and also interfered with the normal reproduction and development of the insect.

Jilani and Saxena, (1990) reported that turmeric oil repelled *Rhyzopertha dominica* and the insect made significantly fewer and smaller punctures in filter paper disks treated with turmeric oil than in the control disks. However, no attempt was made to uncover a specific fraction or compound which is capable of inhibiting insects puncturing.

Lee et al. (2001) reported that ar-turmerone isolated from turmeric was acutely toxic to the storage insects *Sitophilus oryzae, Callosobruchus chinensis, Plodia interpunctella* and *Lasioderma serricorne*.

Su et al. (1982) isolated ar-turmerone and turmerone from turmeric and found that these compounds repelled *T. castaneum*. However, the possibility that any of these compounds might be capable of preventing insect penetration through packaging material was not investigated nor suggested.

U.S. Pat. No. 5,843,215 describes a coating comprising a water-based or water soluble resin and plant secondary compounds including a turmeric derived turmerone.

U.S. Pat. No. 5,688,509 describes a controlled-release insect repellent device for repelling insects from consumable items.

Australian Pat. No. 4,530,499 and Israeli Pat. No. 125,130 describes the use of insect-repelling turmeric extracts in food packaging materials. However, these documents do not describe nor suggest using specific compounds or specific fraction purified from the turmeric extract for that purpose.

While reducing the present invention to practice, the present inventors uncovered that several fractions derived from *Curcuma longa* (turmeric) are capable of preventing pest from penetrating packaging materials by insect repellant and antifeedant activities. The present inventors also uncovered that ar-turmerone is highly effective at preventing pest infestation of packaging materials by repellency, while turmeric sesquiterpene alcohols are highly effective at preventing pest infestation by repellency and antifeedant activities. In addition, a solid residue of turmeric oleoresins, remaining after the removal of the essential oil by liquid extraction, is highly effective at preventing pest infestation by antifeedant activity.

Thus, the present invention provides packaging material which includes sesquiterpene alcohols and/or turmeric oleoresin solid residue and preferably also ar-turmerone at a concentration suitable for preventing pest infestation.

SUMMARY OF THE INVENTION

According to one aspect of the present invention there is provided a composition-of-matter which includes a substance usable in producing packaging material and at least one compound selected from the group consisting an ar-turmerone, sesquiterpene alcohol and a turmeric oleoresin solid residue.

According to another aspect of the present invention there is provided a composition for coating packaging material of packaged goods which includes a substance suitable for coating packaging material and at least one compound selected from the group consisting of ar-turmerone, a sesquiterpene alcohol and a turmeric oleoresin solid residue.

According to yet another aspect of the present invention there is provided a packaged product comprising a product contained within a packaging material modified to include at least one compound selected from the group consisting of ar-turmerone, a sesquiterpene alcohol and a turmeric oleoresin solid residue.

According to still another aspect of the present invention there is provided a method of preventing pest infestation of packaged goods comprising fabricating or modifying packaging material to include at least one compound selected from the group consisting of ar-turmerone, a sesquiterpene alcohol and a turmeric oleoresin solid residue, at a concentration selected capable of preventing pest infestation of goods packaged within the packaging material.

According to an additional aspect of the present invention there is provided a method of producing a pest impervious packaging material comprising modifying a composition used in fabrication of packaging material to include at least one compound selected from the group consisting of ar-turmerone, a sesquiterpene alcohol and a turmeric oleoresin solid residue, followed by using the modified composition to fabricate the packaging material thereby producing the pest impervious packaging material According to yet an additional aspect of the present invention there is provided a pest control composition which includes an effective amount of at least one compound selected from the group consisting of ar-turmerone, a sesquiterpene alcohol and a turmeric oleoresin solid residue.

According to still an additional aspect of the present invention there is provided a packaging material which includes a pest control composition comprising an effective amount of at least one compound selected from the group consisting of ar-turmerone, a sesquiterpene alcohol and a turmeric oleoresin solid residue.

According to yet an additional aspect of the present invention there is provided a method of controlling pest infestation which includes exposing the pest to a composition comprising an effective amount of at least one sesquiterpene alcohol and/or a turmeric oleoresin solid residue.

According to still an additional aspect of the present invention there is provided a pest-impervious sheet which includes at least one layer of a sheet material and at least one compound selected from the group consisting of ar-turmerone, a sesquiterpene alcohol and a turmeric oleoresin solid residue.

According to yet an additional aspect of the present invention there is provided an article-of-manufacturing which includes a container and a pest control composition including an effective amount of at least one sesquiterpene alcohol and/or a turmeric oleoresin solid residue and being identified for the use in pest control.

According to further features in preferred embodiments of the invention described below, the composition-of-matter includes a ratio of the substance usable in producing packaging material to at least one compound selected from the group consisting of ar-turmerone, a sesquiterpene alcohol and a turmeric oleoresin solid residue, which is selected at a range capable of preventing a pest from penetrating the packaging material produced from the composition-of-matter.

According to still further features in the described preferred embodiments the range is selected such that a strength of the packaging material is not substantially different from an identical packaging material produced without at least one compound selected from the group consisting of ar-turmerone, a sesquiterpene alcohol and a turmeric oleoresin solid residue.

According to still further features in the described preferred embodiments the range is selected such that a transparency of the packaging material is not substantially different from an identical packaging material produced without at least one compound selected from the group consisting of ar-turmerone, a sesquiterpene alcohol and a turmeric oleoresin solid residue.

According to still further features in the described preferred embodiments the range is selected such that an elasticity of the packaging material is not substantially different from an identical packaging material produced without at least one compound selected from the group consisting of ar-turmerone, a sesquiterpene alcohol and a turmeric oleoresin solid residue.

According to still further features in the described preferred embodiments the range is selected such that a water permeability of the packaging material is not substantially different from an identical packaging material produced without at least one compound selected from the group consisting of ar-turmerone, a sesquiterpene alcohol and a turmeric oleoresin solid residue.

According to still further features in the described preferred embodiments the range is selected such that a gas permeability of the packaging material is not substantially different from an identical packaging material produced without at least one compound selected from the group consisting of ar-turmerone, a sesquiterpene alcohol and a turmeric oleoresin solid residue.

According to still further features in the described preferred embodiments the pest is an insect or a mite.

According to still further features in the described preferred embodiments the substance usable in producing packaging material is a paper or a paperboard.

According to still further features in the described preferred embodiments the substance usable in producing packaging material is a polymer.

According to still further features in the described preferred embodiments the substance usable in producing packaging material is a textile.

According to still further features in the described preferred embodiments the substance usable in producing packaging material is a metal foil.

According to still further features in the described preferred embodiments the composition for coating packaging material includes a ratio of the substance suitable for coating packaging material to at least one compound selected from the group consisting of ar-turmerone, a sesquiterpene alcohol and a turmeric oleoresin solid residue.

According to still further features in the described preferred embodiments the range is selected such that a strength of the packaging material coated with the composition is not substantially different from the packaging material coated with an identical composition without at least one compound selected from the group consisting of ar-turmerone, a sesquiterpene alcohol and a turmeric oleoresin solid residue.

According to still further features in the described preferred embodiments the range is selected such that a transparency of the packaging material coated with the composition is not substantially different from the packaging material coated with an identical composition without at least one compound selected from the group consisting of ar-turmerone, a sesquiterpene alcohol and a turmeric oleoresin solid residue.

According to still further features in the described preferred embodiments the range is selected such that an elasticity of the packaging material coated with the composition is not substantially different from the packaging material coated with an identical composition without at least one compound selected from the group consisting of ar-turmerone, a sesquiterpene alcohol and a turmeric oleoresin solid residue.

According to still further features in the described preferred embodiments the range is selected such that water permeability of the packaging material coated with the composition is not substantially different from the packaging material coated with an identical composition without at least one compound selected from the group consisting of ar-turmerone, a sesquiterpene alcohol and a turmeric oleoresin solid residue.

According to still further features in the described preferred embodiments the range is selected such that gas permeability of the packaging material coated with the composition is not substantially different from the packaging material coated with an identical composition without at least one compound selected from the group consisting of ar-turmerone, a sesquiterpene alcohol and a turmeric oleoresin solid residue.

According to still further features in the described preferred embodiments, the substance suitable for coating packaging material is a polymer.

According to still further features in the described preferred embodiments, the packaging material of the packaged product is impregnated or coated with at least one compound selected from the group consisting of ar-turmerone, a sesquiterpene alcohol and a turmeric oleoresin solid residue.

According to still further features in the described preferred embodiments, fabricating or modifying the packaging material to include the at least one compound selected from the group consisting of ar-turmerone, a sesquiterpene alcohol and a turmeric oleoresin solid residue, is effected by coating a margin used for welding or gluing the packaging material with a coating substance including at least one compound selected from the group consisting of ar-turmerone, a sesquiterpene alcohol and a turmeric oleoresin solid residue.

According to still further features in the described preferred embodiments the product is a foodstuff.

According to still further features in the described preferred embodiments the at least one compound selected from the group consisting of ar-turmerone, a sesquiterpene alcohol and a turmeric oleoresin solid residue, is included in the packaging material of the packaged product at a concentration selected capable of preventing a pest from infesting the packaged product.

According to still further features in the described preferred embodiments the packaging material is composed of a paper or a paperboard.

According to still further features in the described preferred embodiments the packaging material is composed of a polymer.

According to still further features in the described preferred embodiments the packaging material is composed of a textile.

According to still further features in the described preferred embodiments the packaging material is composed of a metal foil.

According to still further features in the described preferred embodiments the packaging material is composed of a laminate including a plurality of different packaging materials.

According to still further features in the described preferred embodiments fabricating or modifying the packaging material to include at least one compound selected from the group consisting of ar-turmerone, a sesquiterpene alcohol and a turmeric oleoresin solid residue, is effected by coating the packaging material with a laminate containing at least one compound selected from the group consisting of ar-turmerone, a sesquiterpene alcohol and a turmeric oleoresin solid residue.

According to still further features in the described preferred embodiments fabricating or modifying the packaging material to include at least one compound selected from the group consisting of ar-turmerone, a sesquiterpene alcohol and a turmeric oleoresin solid residue is effected by impregnating the packaging material with at least one compound selected from the group consisting of ar-turmerone, a sesquiterpene alcohol and a turmeric oleoresin solid residue.

According to still further features in the described preferred embodiments the pest control composition includes a carrier.

According to still further features in the described preferred embodiments the effective amount of at least one sesquiterpene alcohol and/or turmeric oleoresin solid residue, contained in the pest control composition, is at least 10% on a wt/wt basis.

According to still further features in the described preferred embodiments the effective amount of at least one sesquiterpene alcohol and/or turmeric oleoresin solid residue, contained in the pest control composition is at least 5% on a wt/wt basis.

According to still further features in the described preferred embodiments the effective amount of at least one sesquiterpene alcohol and/or turmeric oleoresin solid residue, contained in the pest control composition is at least 10% on a wt/wt basis.

According to still further features in the described preferred embodiments exposing the pest to the pest control composition is effected by applying the composition using methods such as spraying, soaking, dipping, drenching, mixing, impregnating, fumigating, fogging, coating and dusting.

The present invention successfully addresses the shortcomings of the presently known configurations by providing safe, nontoxic packaging materials impervious to pests which contain at least one compound selected from the group consisting of ar-turmerone, a sesquiterpene alcohol and a turmeric oleoresin solid residue, or analogs, or derivatives thereof, and methods of producing and use of same. In addition, the present invention provides safe, nontoxic pest control compositions, which contain at least one sesquiterpene alcohol and/or turmeric oleoresin solid residue, or analogs, or derivatives thereof, and methods of producing and use of same.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
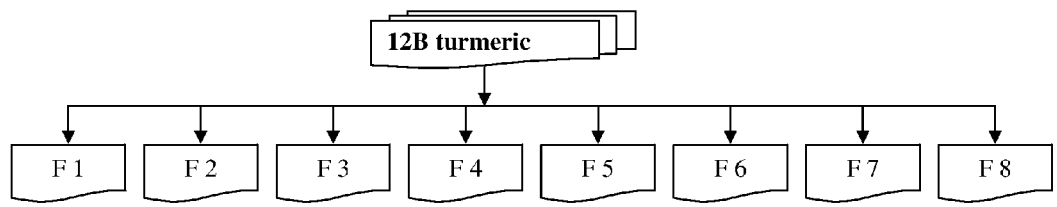
FIG. 1 schematically illustrates the process of separating biologically active fractions from turmeric essential oil 12B by silica gel column chromatography.
Figure 1:
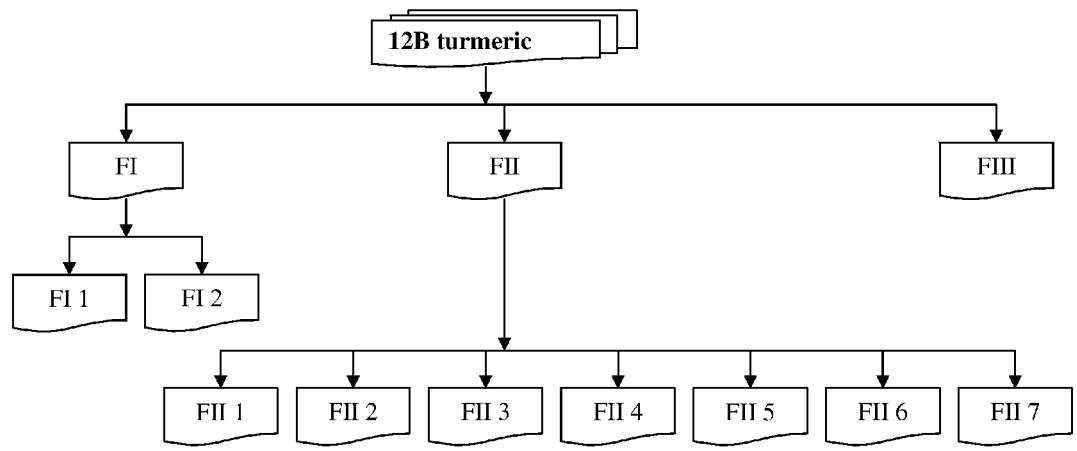

The present invention is of a pest impervious packaging material and a pest control composition which include at least one sesquiterpene alcohol and/or turmeric oleoresin solid residue, or ar-turmerone and at least one sesquiterpene alcohol and/or turmeric oleoresin solid residue, and methods of making and using same.

The principles and operation of a packaging material according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Materials such as polymers, paper or paperboard, textiles and metal foils are all used in producing packaging material for packaging goods. A major drawback of such packaging materials is that pests leading to infestation of the packaged goods can penetrate them. The degree of pest infestation of packaged goods depends upon the pest species involved, the time of exposure to invading pests and the prevailing environmental conditions.

In many instances, synthetic pesticides have been the only effective measure available for controlling pest infestation of stored goods. However, most synthetic pesticides have significant adverse effects on humans and the environment and, accordingly, their use have been substantially excluded from packaged goods such as foodstuffs.

U.S. Pat. No. 5,688,509 describes using various essential oils, such as turmeric essential oil, to repel insects from consumable items. However, this reference does not describe or suggest use of specific constituents of turmeric essential oil, or non-volatile constituents of essential oils, for controlling insect infestation.

The inventors of the present invention disclosed in Australian Pat. No. 4,530,499 and in Israeli Pat. No. 125,130 the use of nontoxic crude extracts of neem or turmeric, capable of repelling insects, to protect packaged foodstuffs from insect infestation, but did not disclose the specific active constituents from the crude extracts. While reducing the present invention to practice the present inventors identified turmeric active fractions, group of compounds and specific compounds which are contained in the above mentioned crude extracts and which are capable of preventing insect penetration through packaging material. In particular, the present inventors surprisingly and unexpectedly uncovered that sesquiterpene alcohols isolated from turmeric oil and which are devoid of ar-turmerone, are highly effective in repelling storage insects, as well as in preventing penetration of storage insects through a treated paper (resulting from an antifeedant activity; see in Example 2 hereinbelow). In addition, the present inventors surprisingly uncovered that turmeric oleoresin solid residue, which remained following a liquid extraction with petroleum ether or diethyl ether, is an effective antifeedant (see Example 4 hereinbelow).

Thus, according to one aspect of the present invention there is provided a composition-of-matter which includes a substance usable in producing packaging material supplemented with at least one compound selected from the group consisting of ar-turmerone, sesquiterpene alcohol and/or turmeric oleoresin solid residue, at a concentration selected capable of preventing pests from penetrating through the packaging material.

The insect repelling feature of ar-turmerone has been previously described. Sue et al. reported in 1982 that ar-turmerone is capable of repelling the storage beetle *Tribolium castaneum* by an average of 62.9% (class IV) as long as 8 weeks following application of this compound. More recently, Lee et al. (2001) reported that ar-turmerone was insecticidal to several field and storage insects, when applied by direct application methods at a concentration of at least 500 ppm.

Figure 2:
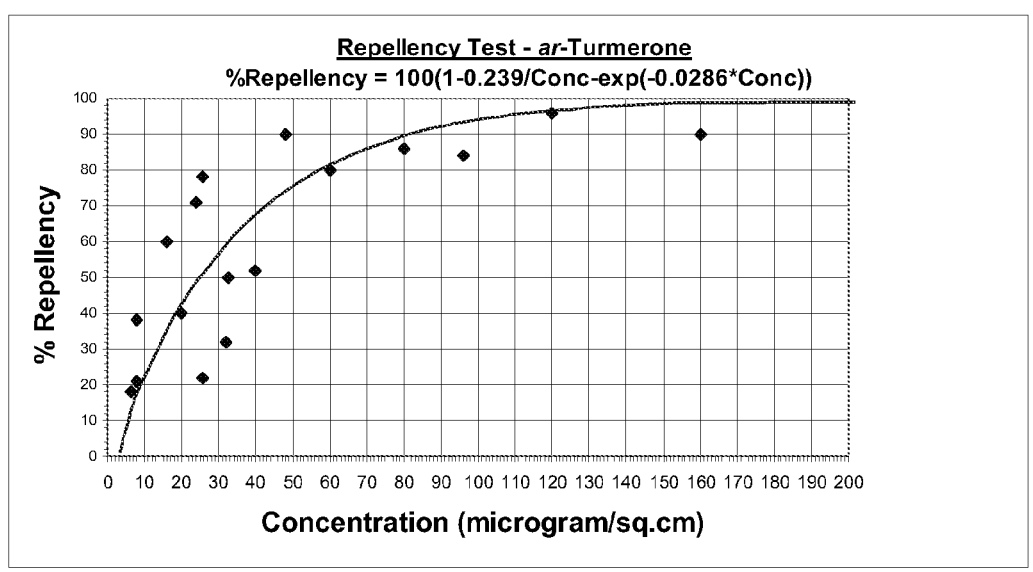
FIG. 2 illustrates the effect of ar-turmerone concentration on repellency of *Tribolium castaneum* adults.

As is illustrated in FIG. 2 and described in Example 2 hereinbelow, ar-turmerone and turmeric fractions containing ar-turmerone effectively prevented storage insects from penetrating through treated paper. The results presented therein further show that the efficiency of turmeric extracts and fractions in preventing penetration was directly related to the concentration of ar-turmerone thus suggesting a central role for this compound in prevention of insect penetration.

Figure 4:
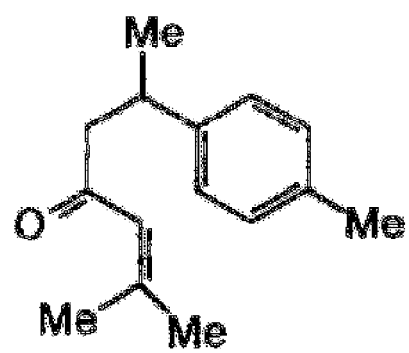
FIG. 4 is a prior art figure illustrating the molecular structure of ar-turmerone as described by He et al. (1998).

The chemical characteristics of ar-turmerone, or 2-methyl-6-(4-methylphenyl)-2-hepten-4-one, were previously described by Rupe et al. (Hely. Chim. Acta. 17:272, 1934), Howard and Rao (Tetrahedron 20: 2921, 1964), Alexander and Rao (Flavour Ind. 4:390, 1973), Khalique and Das (Sci. Res. (Dacca) 5:44, 1968), Crawford et al. (J. Am. Chem. Soc. 94:4298, 1972), Grieco and Finkelhor (J. Org. Chem. 38:2909, 1973), Su et al. (1982) and Aratanechemuge et al. (2002). The molecular structure of ar-turmerone as described by He et al. (1988) is illustrated in FIG. 4.

Ar-turmerone can be purified from turmeric extract by methods such as described by Su et al. (1982) or by Aratanechemuge et al. (2002). Alternatively, ar-turmerone can be synthesized using methods such as that described by Meyers and Smith (Tetrachedron Letters 1979, 2749) or by Sato et al. (Tetrachedron Letters 1980, 3377). Additional methods of isolation of ar-turmerone from turmeric rhizomes or turmeric extract as described hereinbelow.

As described hereinabove, the present inventors uncovered for the first time that sesquiterpene alcohols derived from turmeric are also capable of repelling insects and preventing penetration of insects through a packaging material.

A sesquiterpene alcohol, according to the teaching of the present invention, can be any turmeric sesquiterpene alcohol ($C_{15}$ terpene alcohol) which is capable of repelling insects and/or preventing penetration of insects through a packaging material. For example, a suitable sesquiterpene alcohol can be hinesol, agarospirol, valerianol, β-bisabolol, α-bisabolol, γ-eudesmol, a-turmerol, α-copaen-11-ol, [E]-nerolidol; grossonorol, or tau-cadinol.

Preferably, the present invention utilizes a plurality of sesquiterpene alcohols acting in synergy in repelling insects and/or preventing penetration of insects through a packaging material.

As is illustrated in the Examples section which follows, sesquiterpene alcohols and ar-turmerone can be isolated as enriched fractions from turmeric (*Curcuma longa* L.) rhizomes (underground stems). A turmeric crude essential oil or oleoresin can be prepared by cutting fresh rhizomes into slices, followed by drying and grinding the dry tissue into a powder. The powder is then extracted by way of steam distillation or organic solvent extraction. Solvents like ethanol and acetone are suitable solvents for extraction of turmeric oleoresin. Steam distillation is considered to be the best way to produce the crude oil (turmeric essential oil). Principally, turmeric oil can be produced by liquid extraction, using a non-polar solvent like light petroleum ether or hexane. When turmeric oleoresin is the starting point for obtaining the essential oil, the extraction of the oleoresin with a non-polar solvent, like light petroleum ether, will leave behind the turmeric oleoresin solid residue as a deposit. Once obtained, the crude turmeric oil is fractionated by chromatography methods so as to isolate the fractions containing ar-turmerone and/or sesquiterpene alcohols (target compounds or fractions). A number of chromatography and separation methods can be used, including high-pressure liquid chromatography (HPLC), column chromatography, and distillation under low pressure, all of which are well known in the art. Preferably, the fractionation is effected using a silica gel column-chromatography procedure, such as described in Example 2 and illustrated in FIG. 1. Briefly, turmeric essential oil is applied on top of a silica gel column and eluted with 85:15 (v/v) hexane:ethyl acetate. The eluate is then collected in fractions, followed by removal of the solvent by evaporation. The collected fractions are further analyzed for their chemical composition by gas chromatograph with mass spectrometer (GC/MS), or by other suitable analytical methods known in the art. Fractions exhibiting high concentrations of the target compounds are used as such or selected for repeated, or modified, chromatography steps until containing sufficiently concentrated target compounds. Accordingly, the fractionation described in Example 2 resulted in producing selected turmeric fractions having 30% ar-turmerone (fraction FI-2) or about 50% (estimated) sesquiterpene alcohols (fraction FII).

Thus, ar-turmerone and sesquiterpene alcohols can be isolated from turmeric extracts using separation techniques known in the art. In addition, several of these compounds may be isolated from other plant sources, such as ginger. Alternatively, ar-turmerone and sesquiterpene alcohols, or analogs, or derivatives thereof may be chemically synthesized using methods known in the art, such as described, for example, by Meyers and Smith (Tetrachedron Letters 1979, 2749) or by Sato et al. (Tetrachedron Letters 1980, 3377).

As is mentioned hereinabove, the present inventors also uncovered that turmeric oleoresin solid residue is capable of preventing penetration of insects through a packaging material. The phrase "turmeric oleoresin solid residue" used herein refers to the solid residue which remains following total removal of the essential oil from turmeric oleoresin by liquid extraction. A preferred method of isolating turmeric oleoresin solid residue is described in Example 4 hereinbelow. Thus, according to the teaching of the present invention, ar-turmerone, sesquiterpene alcohols and/or a turmeric oleoresin solid residue can be utilized in preventing pest infestation of packaging materials.

In most cases, packaging materials are selected capable of conferring optimal mechanical and chemical protection to the final packaged product while being cost effective and simple to produce. Several types of substances are used in producing packaging materials including, but not limited to, polymers, papers, paperboards, textiles, metal foils, or any combination thereof.

Polymers used in producing packaging materials may include, for example, polyethylene, polypropylene, polyethylene terephthalate, polyvinyl chloride, polyethylene vinyl chloride, polyethylene dichloride, polyethylene vinyl alcohol, polystyrene, polyethylene vinyl acetate, polyethylene methyl acrylate, polyethylene acrylic acid, polyamide, nylon, or as further described by Brown W. E. (Plastics in Food Packaging, Marcel Dekker Inc., New York, 1992).

Paper products used in packaging material include paper or cardboard composed of natural and/or synthetic fibers and auxiliaries, such as fillers, binders for sizing, retention aids and optical brighteners.

Additional substances used in fabrication of packaging materials include textiles such as cotton or Utah bag and metal foil such as aluminum or tin foil.

Any of the above described substances can be utilized in a composition-of-matter formulated for fabricating pest impervious packaging materials according to the teachings of the present invention.

Such a composition-of-matter can be fabricated by a variety of methods. For example, a composition-of-matter suitable for fabricating polymer based packaging materials, can be generated by mixing ar-turmerone, sesquiterpene alcohols and/or turmeric oleoresin solid residue with polymers as a melt, by solvent compounding, or by immobilization or covalently linking of these compounds to the polymers, see Appendini and Hotchkiss (Innovative Food Science & Emerging Technologies 3: 113-126, 2002) for further description.

A composition-of-matter suitable for fabricating paper based packaging materials, can be generated by adding ar-turmerone, sesquiterpene alcohols and/or turmeric oleoresin solid residue, to a paper pulp emulsion or impregnating paper, paperboard or textile substances with these compounds using methods well known in the art (e.g., spraying, dipping).

A composition-of-matter suitable for fabricating flexible packaging materials, composed mainly of laminates, can be generated by adding ar-turmerone, sesquiterpene alcohols and/or turmeric oleoresin solid residue to any adhesive or ink or lacquer or any other additive between the laminate layers or to any coating on the laminate. Preferably, the ratio of ar-turmerone, sesquiterpene alcohols and/or turmeric oleoresin solid residue and the substance used in producing a packaging material is selected at a range capable of preventing a pest, preferably an insect or a mite, from penetrating the packaging material. In addition, the range is preferably selected such that the physical qualities of the resultant packaging material (e.g., strength, elasticity, transparency, water permeability or gas permeability) is not substantially different from an identical packaging material produced without ar-turmerone, sesquiterpene alcohols and/or turmeric oleoresin solid residue.

The preferred ratio of ar-turmerone, sesquiterpene alcohols and/or turmeric oleoresin solid residue to the substance usable in producing packaging material is dependent on the physical and chemical properties of the substance and on the target pest(s). Preferably, the level of ar-turmerone, sesquiterpene alcohols and/or turmeric oleoresin solid residue in the packaging material should be sufficiently high so as to effectively and reliably render pest resistance, while, on the other hand, being sufficiently low so as not to substantially weaken, or otherwise substantially alter the physical properties of the packaging material.

The lowest effective concentration of ar-turmerone, sesquiterpene alcohols and/or turmeric oleoresin solid residue in the packaging material which can confer pest resistance can be determined on a case by case basis using pest-penetration bioassays such as described by Navarro et al. (1998) and in full details in Example 2 of the Examples section which follows. Briefly, the test packaging material is cut into small discs or strips which are impregnated with different concentrations of ar-turmerone, sesquiterpene alcohols and/or turmeric oleoresin solid residue. The treated pieces of packaging material are tested for repellency and penetration prevention efficiency in the repellency, choice non-choice bioassays as described in Example 2. The highest concentration of ar-turmerone, sesquiterpene alcohols and/or turmeric oleoresin solid residue utilizable in the packaging material while maintaining desirable physical properties can be determined by standard test methods well known in the art.

Thus, the preferred ratio of ar-turmerone, sesquiterpene alcohols and/or turmeric oleoresin solid residue and the substance usable in producing packaging material, in the composition-of-matter of the present invention, is selected at a range capable of preventing a pest from penetrating the packaging material, while at the same time not substantially altering the desired physical properties of the packaging material.

Preferably, the concentration of ar-turmerone used in the packaging material of the present invention is selected from a concentration range of 0.1 to 0.5 $g/m^2$, while the concentration of sesquiterpene alcohols used in the packaging material of the present invention is selected from a concentration range of 0.03 to 0.2 $g/m^2$ and the concentration of the turmeric oleoresin solid residue used in the packaging material of the present invention is selected from a concentration range of 0.1 to 0.5 $g/m^2$.

The composition-of-matter of the present invention may further include processing additives or additives that facilitate use of the package, for example heat stabilizers, slip additives, preservatives or components for control of unwanted growth such as antimicrobial agents. Antimicrobial agents which may be utilized in producing a packaging material in accordance with the present invention are disclosed and described in detail in U.S. Pat. Nos. 3,044,885, 3,493,464, 3,653,873, 3,728,213, 3,864,468, 3,959,556, 3,998,944, 4,008,351, 4,111,922, 4,343,853, 4,401,712, 4,533,435, 4,663,077, 4,666,706, 4,743,448, 4,888,175, 5,242,052; and by Appendini and Hotchkiss (Innovative Food Science & Emerging Technologies 3: 113-126, 2002).

Fabrication of packaging materials using the composition-of-matter of the present invention can be effected using a variety of well-known methods. For example, a polymer-based composition-of-matter can be formed into various shapes of packages such as bags, boxes and transparent liners, through processes such as extrusion, molding, foaming, casting, or dipping.

In an extrusion process, a melted polymer is forced through an orifice with a particular cross section (die) and a continuous shape is formed with a constant cross section similar to that of the orifice. For some applications, laminated structures may be made by extruding more than one composition-of-matter at the same time through the same die or through multiple dies. Multilayer laminates are particularly advantageous for food packaging since the outer layers may contribute strength and moisture resistance while the inner layers may contribute oxygen permeability.

In a molding process, a molding powder, or pellet, of the composition-of-matter can be heated and at the same time compressed into a specific shape. Alternatively, it can be injected from one heated apparatus, to another apparatus which remain cold, for shaping and cooling (injection molding). The polymer composition-of-matter can also be formed into a tube, then sealed in one hand, blown and expanded in a split mold with a cold surface. As it encounters the surface, the heated composition cools off and becomes dimensionally stable.

Packages made of paper and paperboard-based compositions-of-matter can be readily manufactured, by way of cutting, pasting, folding and/or joining into a great variety of shapes and sizes.

Packages made of multilayer laminates composed of more than one layer of material such as plastics (polymer), aluminum foil, paper or board can be readily manufactured by way of using an adhesive between layers. The layers may be identical or differing materials, such as different polymers, a polymer with a paper or a polymer with aluminum foil.

Pest impervious packaging materials can also be fabricated by adding, dissolving or dispersing ar-turmerone, sesquiterpene alcohols and/or turmeric oleoresin solid residue in the adhesive or ink or lacquer or any other additive between the layers of multilayer laminates used as ordinary packaging materials.

Pest impervious packaging materials can also be fabricated by coating ordinary packaging materials with a coating composition which includes ar-turmerone, sesquiterpene alcohols and/or turmeric oleoresin solid residue.

Thus, according to another aspect of the present invention, there is provided a composition for coating packaging material of packaged goods which include a substance suitable for coating packaging material and ar-turmerone, sesquiterpene alcohols and/or turmeric oleoresin solid residue.

Coating substances which can be applied to a packaging material include, but not limited to, a lacquer, a varnish, a paint, or a film.

Paper or paperboard packaging materials are typically coated with a composition suitable for printing high quality graphics. Coating compositions useful for printing high quality graphics generally include a fluidized blend of minerals such as coating clay, calcium carbonate, and/or titanium dioxide with a suitable binder such as starch, or resins such as polyvinyl alcohol, polystyrene or the like. These coating compositions are generally applied to paperboard substrates on a paper machine during the papermaking process by typical coating devices such as roll, rod, air-knife or blade coaters.

Alternatively, paper, paperboard, polymers, foils, or other packaging materials can be coated with a liquid-tight film composed of a polymer substance. Preferably, the polymer is an extrudable resin, polyethylene, polypropylene, polyethylene terephthalate, acrylics, polyethylene vinyl chloride, or polyvinylidene chloride. Optionally, specialized controlled-atmosphere coating compositions can be used, such as described, for example, in U.S. Pat. Nos. 4,842,875, 4,879,078, 4,910,032, 4,923,650, 5,011,698, 5,045,331, 5,160,768, 5,254,401, and 6,190,710.

Alternatively, or additionally, the pest impervious packaging material of the present invention includes a margin used for welding or gluing the packaging material with a coating or adhesive substance which includes at least one compound selected from the group consisting of ar-turmerone, a sesquiterpene alcohol and a turmeric oleoresin solid residue.

The coating material of the present invention can be produced by dissolving ar-turmerone, sesquiterpene alcohols and/or turmeric oleoresin solid residue, at a desired concentration, in the solution, suspension, emulsion or melt of the coating composition, or by solvent compounding. Alternatively, a coating material can be modified by adsorbing or by ionic or covalent linking of the coating composition to ar-turmerone, sesquiterpene alcohols and/or turmeric oleoresin solid residue, at a desired concentration, using methods such as described by Appendini and Hotchkiss (Innovative Food Science & Emerging Technologies 3:113-126, 2002).

The turmeric compounds ar-turmerone, sesquiterpene alcohols and turmeric oleoresin solid residue may also be utilized to produce a pest-impervious sheet for use in agriculture (e.g., soil mulching, tunnels, greenhouses) and industry (e.g., storing and shipping goods).

Thus, according to another aspect of the present invention, there is provided a pest-impervious sheet which includes a sheet material and at least one compound selected from the group consisting of ar-turmerone, sesquiterpene alcohols and turmeric oleoresin solid residue.

As used herein the term "sheet" refers to any broad flat thin piece of material such as, for example, a film.

A suitable sheet material may include a polymer, a paper, a paperboard, a textile and/or a metal foil. Preferably, the sheet material further includes ar-turmerone, sesquiterpene alcohols and/or turmeric oleoresin solid residue. Alternatively, or additionally, the sheet material is coated with a substance, which includes ar-turmerone, sesquiterpene alcohols and/or turmeric oleoresin solid residue. A suitable pest-impervious sheet can be a monolayer sheet or a multilayer sheet (a laminate). Preferably, the laminate includes ar-turmerone, sesquiterpene alcohols and/or turmeric oleoresin solid residue contained in adhesive between the layers.

As is mentioned hereinabove, sesquiterpene alcohols and turmeric oleoresin solid residues have not been known previously to have any effect on insect behavior. While reducing the present invention to practice, and as further described in the Examples section that follows, the present inventors have surprisingly uncovered that these substances were highly effective in preventing insect penetration through a treated paper.

Thus, according to another aspect of the present invention there is provided a pest control composition, which includes an effective amount of at least one sesquiterpene alcohol and/or a turmeric oleoresin solid residue. Preferably, the pest control composition further comprises a carrier, such as a liquid carrier or a solid carrier.

The term "carrier" used herein refers to an inert material, which may be inorganic or organic and of synthetic or natural origin, with which the active compound is mixed or formulated to facilitate its application, or its storage, transport and/or handling.

A suitable liquid carrier may include, but not limited to, aromatic hydrocarbons (e.g. benzene, toluene, xylene, alkyl naphthalenes, etc.), halogenated especially chlorinated, aromatic hydrocarbons (e.g. chloro-benzenes, etc.), cycloalkanes, (e.g. cyclohexane, etc.). paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide etc.) sulfoxides (e.g. dimethyl sulfoxide, etc.), acetonitrile, ketones (e.g. acetone, methyl ethyl ketone, methyl isobutyl ketone, cyclohexanone, etc.), natural oils, and/or water A suitable solid carrier may include, but not limited to, natural mineral powders, such as kaolin, clay, talc, chalk, chalcedony, attapulgite, montmorillonite, and diatomite; synthesized mineral powders, such as silicic acid, alumina, and silicate; and polymeric natural products, such as crystalline cellulose, cornstarch, gelatine, and alginic acid. One or a mixture of two or more of these carriers can be used.

In addition, the pest control composition of the present invention may include a surfactant, such as but not limited to, polyoxyethylene-fatty acid ester, polyoxyethylene-fatty alcohol ether, alkylaryl polyglycol ether, alkylsulfonate, alkylsulfate, and arylsulfonate. Optionally, the pest control composition of the present invention may include an emulsifier, a dispensing agent, and/or an adjuvant such as carboxymethyl cellulose, polyoxyethyleneglycol, gum Arabic, starch, and lactose.

Preferably, the pest control composition of the present invention contains at least 5%, preferably at least 10% of at least one sesquiterpene alcohol and/or turmeric oleoresin solid residue, on a wt/wt basis.

The pest control composition of the present invention is intended for use in controlling infestation of pests, such as storage pests, household pests and/or agricultural pests. As such, the pest control composition according to this aspect of the present invention can be utilized in fabrication or coating of packaging materials as is described hereinabove, or it can be directly used to control pests. For example, pests can be directly exposed to sesquiterpene alcohols and/or turmeric oleoresin solid residue compositions using application approaches such as, for example, spraying, soaking, dipping, drenching, mixing, impregnating, fumigating, coating or dusting.

Preferably, the pest control composition of the present invention is kept in a suitable container as an article-of-manufacturing and identified for use in pest control.

Hence, the present invention provides safe, nontoxic packaging materials impervious to pests which contain ar-turmerone, one or more sesquiterpene alcohols and/or turmeric oleoresin solid residue, or analogs, or derivatives thereof, and methods of producing and use of same. In addition, the present invention provides safe, nontoxic pest control compositions and articles-of-manufacturing which contain sesquiterpene alcohols and/or turmeric oleoresin solid residue, or analogs, or derivatives thereof, and methods of producing and use of same.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Example 1

Turmeric Induced Insects' Repellence and Penetration Prevention

Materials and Methods:

Turmeric extracts: Powdered turmeric rhizomes (underground stems) were imported from India and Bangladesh. The rhizomes from India were purchased in the Israeli market and known as freshly imported rhizomes from India, the Bangladesh rhizomes were purposely imported from Allied Agro Industries, Baridhara, Dhaka in Bangladesh, One kilogram of the powder was extracted in Soxhlet extractors with petroleum ether (boiling point 40-60° C.) for 4 hours. The petroleum ether was removed in a rotary evaporator under reduced pressure to obtain the crude turmeric essential oil extract.

Additional turmeric essential oils were obtained from the USA (12A and 12B) and India (Suthar and Kancor). An oleoresin (E4) was obtained from India (Synthite in Cochin).

Insects: The test insects were adults of the lesser grain borer, *Rhyzopertha dominica* F. and the red flour beetle, *Tribolium castaneum* (Herbst.). Both species were reared on a mixture of broken wheat and 5% yeast (by weight). Cultures were kept at 27° C. and 65% R.H and the emerging adults of both species were separated from rearing cultures at two-week intervals, and then held in pre-treatment jars at 27° C. and 65% R.H until they were 7-21 days old.

Repellency Bioassay: The propensity of the tested extracts to repel insects was determined against *T. castaneum* and *R. dominica* adults using the methods described by Laudani et al. (1955) and McDonald et al. (1970). Accordingly, filter paper strips (Filtrak 3 HW; 10×20 cm) were treated with 4 ml of acetone solutions of turmeric extracts, at dosage of 800 µg/cm$^2$ on the paper. Each treated paper strip was attached lengthwise edge to edge, by Scotch tape on the reverse side, to two untreated 5×20 cm strips, to which acetone alone had been similarly applied. Two glass rings, 2.5 cm high and 6.4 cm i.d., were then placed over the two matched papers so that the joined edges of the papers bisected the rings. Ten adults of each insect species, were then exposed separately on the test arenas inside each glass ring, and their numbers on the treated and untreated halves were recorded after one hour and after eight hours exposure on the first day, and then at 9 a.m. and 4 p.m. each day for 5 consecutive days. All tests were run at 27° C. and 65% R.H. and each test was repeated four times. The average counts over each 5-day period were converted to percent repellency, as described by Laudani et al. (1955). Results were assigned a repellency class by using the following scale: Class 0, <0.1%; class I, 0.1-20%; class II, 20.1-40%; class III, 40.1-60%; class IV, 60.1-80%; class V, 80.1-100%.

Non-choice penetration prevention bioassay: The device used for the penetration prevention bioassay consisted of two identical open-ended glass cylinders (24 mm i.d., 28 mm o.d., 26 mm height) each with four notches spaced at equal distances around the outer rim. The impregnated office paper and a piece of wire-mesh (US standard No. 25) cut into 28 mm diameter discs were placed together on top of one cylinder. Then the second cylinder was placed over the wire-mesh and the two cylinders were pressed together and held in place by two rubber bands, secured by the notches in the cylinder rims (Navarro et al., 1998). Ten 10-15 d old *R. dominica* adults were placed inside the top cylinder and were kept in the test devices for 24 in a temperature and humidity controlled room. All tests were run at 27° C. and 65% R.H., and there were ten replicates (devices) per test. At the end of each exposure period, the discs were examined on a black surface under a binocular microscope at 15× magnification. The number of perforations appearing as black circles were counted, and a comparative analysis was performed using the Student's t test for residual effect and the differences between control and dosages applied were determined using Dunnet's test (Anon., 1989). The resulting preventing penetration efficacy (PPE) of the different turmeric extracts, or fractions thereof, were classified as low (0-40% PPE), medium (40-80% PPE), or high (80-100% PPE).

White office printer paper (80 g/m$^2$, 110 µm thick) was selected as the test material after preliminary tests revealed its low resistance to penetration by *R. dominica* adults. The paper was cut into 28 mm diameter discs, which were treated with 100 µl acetone solutions of turmeric extract at different dosages of 50 to 2560 µg/cm$^2$. Paper discs treated only with 100 µl acetone served as control. Following application of test solutions the acetone solvent was evaporated to dryness in a hood. The treated paper discs were kept at 27° C. and 65% R.H until used in the bioassay. Penetration prevention bioassays were carried out at delays of 1, 15, 30, 45, 60, and 75 days after treatment, or for as long as the treatment remained effective.

Results:

Insect repellency: The extracts of turmeric essential oils from turmeric rhizomes originated in Bangladesh and India (Israeli market) induced repellency class III and IV with both test insects, *T. castaneum* and *R. dominica*, thereby showing that the turmeric extracts contained highly effective insect-repelling substance(s).

Insect penetration prevention: Essential oil from turmeric extract, applied to paper discs at a dosage of 640 µg/cm$^2$, substantially reduced penetration by *R. dominica*, up to 60 days. Higher turmeric extract dosages of 1280 µg/cm$^2$ and 2560 µg/cm$^2$ resulted in extended periods of protection of over 75 days.

Table 1 below shows that essential oils prepared from rhizomes by extraction with petroleum ether, or steam distillation, resulted in several cases in high penetration prevention efficiency (PPE) of 80-100%, demonstrating the high penetration prevention efficiency of these oils. The other turmeric extracts provided, apparently, medium or low PPE in the non-choice test. As the non-choice test results are also influenced by the repellency effect which acts in this test in the reversed direction (as explained in Example 2), it is expected that all of the cited essential oils have quite strong antifeedant (penetration prevention) effect, as all of them showed quite a strong repellency. Nonetheless, the results indicate that the source of turmeric rhizomes, as well as the particular extraction method used, substantially affected the biological activity of turmeric extracts.

TABLE 1

Insect penetration prevention efficacy of turmeric extracts

| Source of material | Extraction method | PPE[2] |
|---|---|---|
| Rhizomes from Bangladesh | Petroleum ether[1] | High |
| Rhizomes from India (market) | Petroleum ether[1] | Medium |
| Essential oil from the USA (12A) | Steam distillation (by producer) | High |
| Essential oil from the USA (12B) | Steam distillation (by producer) | High |
| Essential oil from India-Suthar | Steam distillation (by producer) | Low |
| Essential oil from India-Kancor | Steam distillation (by producer) | High |
| Oleoresin (E4) from India-Synthite | Oleoresin extract (by producer) | Medium |

[1]Powdered turmeric rhizomes were extracted in a Soxhlet extractor with petroleum ether (boiling point 40 to 60° C.) for 4 h.
[2]PPE: penetration prevention efficacy was classified as Low when insect penetration was reduced by 0-40%, Medium when insect penetration was reduced by 40-80% and High when insect penetration was reduced by 80-100%.

Example 2

Turmeric Induced Insects' Repellency and Penetration Prevention

Materials and Methods:

ar-turmerone: S-(+)-ar-turmerone 80% was purchased from Botanix Limited, Kent, England.

Turmeric essential oil: Turmeric essential oils were obtained from the USA (12A and 12B).

Insects: The test insects were adults of the lesser grain borer *Rhyzopertha dominica* and the red flour beetle *Tribolium castaneum* (Herbst). Both species were reared on a mixture of broken wheat and 5% yeast (by weight). Cultures were kept at 27° C. and 65% R.H and the emerging adults were separated from rearing cultures at two-week intervals and were then held in pre-treatment jars at 27° C. and 65% R.H until they were 7-21 days old.

Thin layer chromatography (TLC): Samples of turmeric oils and extracts were spotted on a 20×20 cm pre-coated Alugram silica-gel aluminum backed plates with fluorescent UV indicator (Macherrey-Nagel, Germany). The plates were developed in 85:15 hexane:ethyl acetate. The separated components were visualized under UV at 254 nm and by spraying with vanillin aldehyde in sulfuric acid. Since the amount of material which could be obtained from the TLC bands was insufficient for performing bioassays, selected turmeric oil was subsequently fractionated by silica gel column chromatography, yielding fractions in sufficient amounts for bioassays and GC/MS analysis.

Silica gel column chromatography: Glass columns of 75 cm long and 1 cm in diameter were packed with silica gel powder and covered with 1 cm layer of pure sea sand. Each 1.25 ml portion of the chosen turmeric essential oil was then applied on top of a column and eluted with 85:15 (v/v) hexane:ethyl acetate solution provided at 8 drops per minute. Several fractions were collected and solvent removed in a rotary evaporator under reduced pressure. Biologically active fractions were farther separated into sub-fractions by the same procedure of column chromatography.

GC/MS analysis: The chemical composition of the turmeric essential oil (12B) and its fractions was determined using a GC/MS system (Agilent Technologies)-HP MSD 5973 mass spectrometer (70 eV, electron impact ionization), coupled with a HP 6890 GC. The GC was equipped with a 30 m×0.25 mm×0.25 μm Restek Rtx-5SIL MS capillary column. Helium was used as a carrier gas (0.8 ml/min). Temperature was held at 50° C. for 1 min and raised to 290° C. at 5° C./min. The injector temperature was 250° C. A 1 μl of diluted sample in acetone or methyl tributyl ether was injected in the split mode. Simultaneous injections of n-alkanes standards were performed to enable the determination of Kovat's retention indices of the chemical constituents. Identification of the chemical substances was based on using the HP data processing system, the NIST search engine and the following mass spectra data bases: (i) HPCH1607-based on mass spectra and Kovat's retention indices [R. P. Adams (Ed.), "Identification of Essential Oil Components by Gas Chromatography/Quadruple Mass Spectrometry", Allured Pub. Co. (2001)]; (ii) NISTO2 (NIST Rev. D.04.00, October 2002); and (iii) Flavor2 (HP Flavors library). Quantification was based on comparison of integrated peak areas.

Repellency and penetration prevention bioassays—rational: In order to evaluate the effect of isolated samples or compounds on the behavior of storage insects, three bioassays were conducted: repellency, "choice" and "non-choice" paper perforation bioassays. These bioassays were aimed to uncover two principle activities: repellency and antifeedant activities. Accordingly, the "repellency bioassay" uncovered the sample's capacity to repel insects and the "choice bioassay" uncovered the combined antifeedant and repelling activities. In the "non-choice bioassay" a repelling activity resulted in increased perforation, while an antifeedant activity resulted in decreased perforation. Thus, the combined data of all three bioassays enabled determining the antifeedant capacity of the sample. Since, under the experimental conditions, sample concentration directly affected insect activity, the bioassays were performed within a concentration range which exhibited varying levels of insect activities in the bioassays. When a sample exhibited repellency activity which was higher than its antifeedant activity, the "choice bioassay" resulted in a positive value, while the "non-choice bioassay" resulted in a negative value. On the other hand, when a sample exhibited repellency activity which was lower than its antifeedant activity, the "non-choice bioassay" resulted in a positive value.

Repellency Bioassay procedure: The propensity of the tested extracts to repel insects was determined against *T. castaneum* adults using the methods by Laudani et al. (1955) and McDonald et al. (1970). Accordingly, filter paper strips (Filtrak 3 HW; 10×20 cm) were treated with 4 ml of acetone solutions of turmeric extracts at 50 $\mu g/cm^2$ (or any other predetermined concentration). Each treated paper strip was attached lengthwise by Scotch tape on the reverse side, edge to edge, to two untreated 5×20 cm strips, to which acetone alone had been similarly applied. Two glass rings, 2.5 cm high and 6.4 cm i.d., were then placed over the two matched papers so that the joined edges of the papers bisected the rings. Ten adults of the test insect species were then exposed separately on the test arenas inside each glass ring, and their numbers on the treated and untreated halves were recorded every hour for the first eight hours exposure on the first day, and then in the morning of the next day two additional recordings were made for a total of 10 consecutive readings. In each test four replicates were conducted. All tests were performed at 27° C. The average count of all four replicates, each containing 10 reading periods was converted to percent repellency values, as described by Laudani et al. (1955).

"Non-choice" bioassay procedure: White office printer paper (80 g/$m^2$, 110 μm thick) was selected as the test material after preliminary tests revealed its low resistance to penetration by *R. dominica* adults. The paper was cut into 28 mm diameter discs which were treated with 100 μl acetone solutions of turmeric extract at dosages of 50 and 640 $\mu g/cm^2$ in the routine evaluation tests (Other dosages of 64, 100, 160, 200, 320, 1280, and 2560 were also tested in special experiments). Paper discs treated only with 100 μl acetone served as control. Following application of test solutions the acetone solvent was evaporated to dryness in a hood. The treated paper discs were used in the bioassay on the next day, which was carried for 24 hours.

"Choice" bioassay procedure: The same methodology used in the non-choice test was used in this test. However, in choice test, the 28 mm diameter discs of 110 μm thick office paper were divided in half; one side was impregnated with the oil or fraction under test, while the other half was used as a blank and was treated with acetone only. In this test only a 50 microgram sample of the test oil or fraction was applied per $cm^2$ of paper. The test insects were entrapped on the paper and could choose to perforate the blank, perforate the impregnated part of the paper, or not to perforate any part. At the end of each exposure period, the discs were examined. The number of perforations appearing in the two parts of the disc were counted, and a comparative analysis was performed using the Student's t test for residual effect and the differences between control and dosages applied were determined using Dunnet's test (Anon., 1989). For example, if the insects did not perforate the impregnated part of the paper (only the untreated part) and the results of repellency showed that the tested oil or fraction had low repellent efficiency it was then concluded that the sample contained antifeedant components.

Results:

TLC analysis of turmeric extracts: TLC analysis of turmeric USA essential oil 12A gave 7 distinct bands. A further GC/MS analysis of the TLC bands putatively identified the presence of the main components of turmeric oil. Due to insufficient amount of the components for bioassays, the results could not be further investigated. Yet, the TLC and preliminary GC/MS analysis were the basis for the silica gel column chromatography fractionation.

Column chromatography fractionation: Turmeric USA essential oil 12B was obtained from the same supplier as 12A and had similar biological activity. The turmeric essential oil 12B was fractionated on a silica gel column chromatography to four main fractions and seven sub-fractions of the more biologically active fraction FII, as illustrated in FIG. 1. An 18 g sample of 12B crude oil was fractionated in portions on several columns with a total recovery of about 69% and fractions weight of 3.7, 6.3, 1.2 and 1.2 g for fractions FI-1, FI-2, FII and FIII, respectively.

Figure 3:
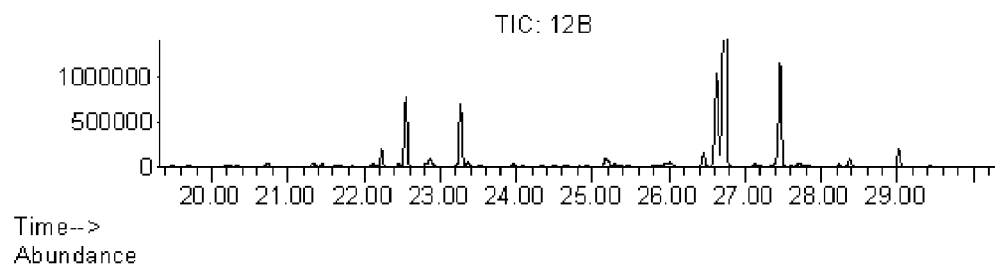
FIG. 3 illustrates TIC chromatograms of GC/MS analyses of turmeric essential oil 12B and fractions thereof, obtained by silica gel column chromatography.
Figure 3:
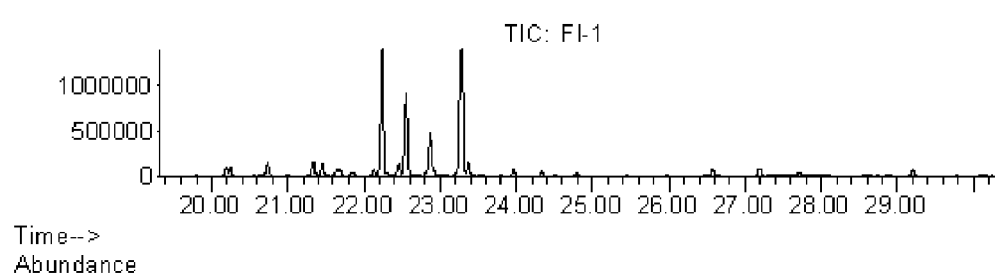
Figure 3:
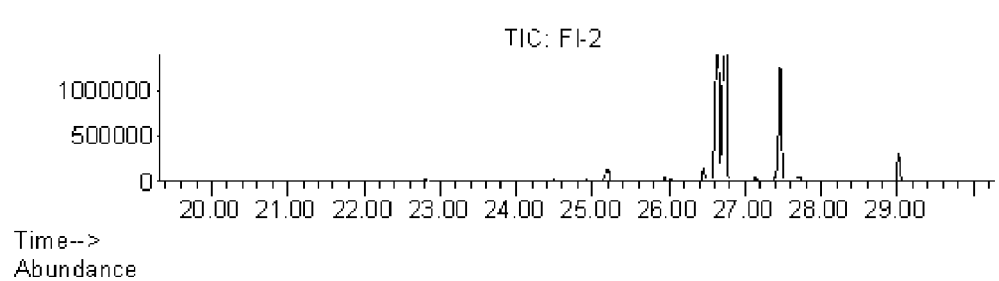
Figure 3:
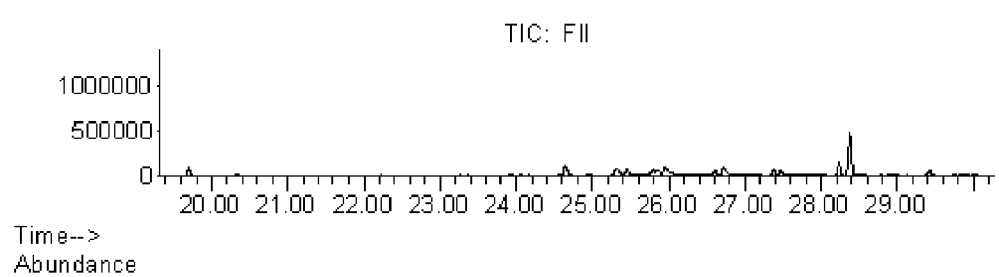
Figure 3:
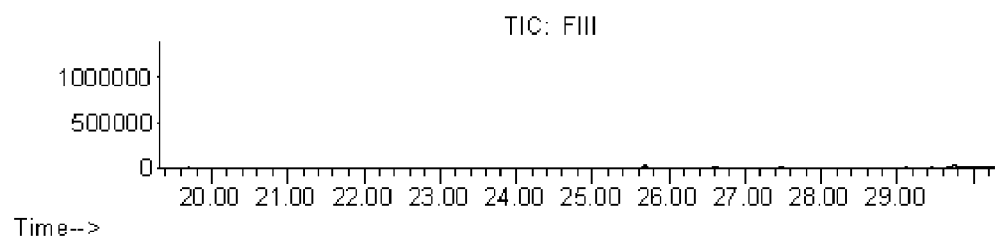

GC/MS analysis: GC/MS analyses of the four main fractions and crude turmeric oil 12B indicated that the fractionation on the silica gel columns gave really an effective separation of the fractions. The main part of the TIC (total ion current) chromatograms of 12B and its four fractions is illustrated in FIG. 3. The chemical compositions identified in the major peaks in the TIC chromatograms of FI-1, FI-2 and FII fractions are presented in Tables 2, 3 and 4. The GC/MS analyses indicate that most prominent compounds concentrated in a single fraction, with certain monoterpenes and aromatic oxygenated and non-oxygenated terpenes in non-negligible amounts in more than a single fraction. Accordingly, ar-turmerone (an aromatic sesquiterpene ketone) concentrated mainly in the FI-2 fraction (30% of the fraction) and was also found in the FII and FIII fractions in small amounts (1.7 and 0.75%, respectively). ar-curcumene (an aromatic sesquiterpene) concentrated mainly in the FI-1 fraction (18.6% of the fraction), with minor amount found in fraction FI-2 (0.09%). P-cymene (an aromatic monoterpene) concentrated mainly in fraction FI-1 (4.9%) and was also found in FI-2 and FII fractions (0.39 and 0.22%, respectively). α-phellandrene (a monoterpene) concentrated mainly in fraction FI-1 (2.5%) and was also found in fraction FI-2 (0.58%).

The identities and concentrations of major components found in fraction FI-1 and in the crude oil 12B are shown in Table 2 below. The FI-I fraction was mainly composed of pure sesquiterpenes $C_{15}H_{22}$ and $C_{15}H_{24}$. In addition, fraction FI-I included several monoterpenes, p-cymene being the most prominent one. In addition, fraction FI-1 contained 3 unidentified oxygenated compounds in minor concentrations (total of <3%).

TABLE 2

Identities and concentrations of major compounds in turmeric oil 12B and in fraction FI-1 determined by GC/MS analysis

| # | Compound | RT (min) | Concentration in 12B (%) | Concentration in FI-1(%) |
|---|---|---|---|---|
| 1 | α-phellandrene | 9.12 | 2.8 | 2.5 |
| 2 | p-cymene | 9.68 | 0.74 | 4.9 |
| 3 | [E]-caryophyllene | 20.74 | 0.44 | 1.7 |
| 4 | $C_{15}H_{22}$ (similar to thujopsadiene) | 21.34 | 0.51 | 1.9 |
| 5 | [Z]-β-farensene | 21.46 | 0.35 | 1.6 |
| 6 | γ-curcumene | 22.13 | 0.47 | 0.8 |
| 7 | ar-curcumene | 22.23 | 2.0 | 18.6 |
| 8 | unidentified $C_{15}H_{22}$ | 22.46 | 0.28 | 1.6 |
| 9 | α-zingiberene | 22.55 | 8.1 | 10.3 |

TABLE 2-continued

Identities and concentrations of major compounds in turmeric oil 12B and in fraction FI-1 determined by GC/MS analysis

| # | Compound | RT (min) | Concentration in 12B (%) | Concentration in FI-1(%) |
|---|---|---|---|---|
| 10 | β-bisabolene | 22.87 | 1.1 | 5.8 |
| 11 | β-sesquiphellandrene | 23.27 | 7.1 | 22.0 |
| 21 | [E]-γ-bisabolene | 23.36 | 0.56 | 1.7 |

The identities and concentrations of major components found in fraction FI-2 and in the crude oil 12B are shown in Table 3 below. Fraction FI-2 was mainly composed of sesquiterpene ketones $C_{15}H_{20}O$ and $C_{15}H_{22}O$ and also included pure monoterpenes (α-phellandrene, p-cymene) and oxygenated monoterpenes (like eucalyptol) in very low concentrations.

TABLE 3

Identities and concentrations of major compounds in turmeric oil 12B and in fraction FI-2 determined by GC/MS analysis

| # | Compound | RT (min) | Concentration in 12B (%) | Concentration in FI-2 (%) |
|---|---|---|---|---|
| 1 | α-phellandrene | 9.12 | 2.8 | 0.58 |
| 2 | 3 unidentified | 25.20 | ~1.6 | 2.5 |
| 3 | $C_{15}H_{22}O$ (similar to curlone) | 25.95 | 0.59 | 0.51 |
| 4 | $C_{15}H_{22}O$ (similar to turmerone) | 26.46 | 1.7 | 1.8 |
| 5 | ar-turmerone | 26.64 | 12.7 | 29.9 |
| 6 | turmerone | 26.74 | 29.6 | 33.1 |
| 7 | [Z]-γ-atlantone | 27.14 | 0.52 | 0.62 |
| 8 | Curlone | 27.46 | 12.9 | 17.1 |
| 9 | [Z]-α-atlantone | 27.71 | 0.53 | 0.73 |
| 10 | [E]-α-atlantone | 29.02 | 2.0 | 3.8 |

As illustrated in FIG. 3, fractions FI-1 and FI-2 contained relatively few components in relatively high concentrations, while fraction FII contained a relatively large number of compounds in relatively small concentrations. Facing this complexity and the fact that the FII fraction was particularly active biologically (as shown in Table 5 below) this fraction was further separated into 7 sub-fractions, FII-1 to FII-7, using the same silica gel column chromatography procedure.

The identities and concentrations of major components found in fraction FII, its sub-fractions and in crude oil 12B are shown in Table 2 below. Accordingly, fraction FII included the followings: (i) sesquiterpene ketones $C_{15}H_{22}O$ and $C_{15}H_{24}O$, the main one α-oxobisabolene, including also at least one $C_{14}H_{22}O$ (formally not a terpenoid derivative); (ii) sesquiterpene alcohols, including phenols like curcuphenol, $C_{15}H_{22}O$ (ar-tumerol, curcuphenol), $C_{15}H_{24}O$ and $C_{15}H_{26}O$; (iii) some other compounds, for example an aromatic hydrocarbon $C_{13}H_{20}$ (non-terpenoid).

As can be seen in Table 4 below, the major components identified in fraction II composed only about 56% of the FII content (as estimated from peaks area). The remaining part of fraction FII mainly consisted of identified and unidentified sesquiterpene alcohols in relative low concentration, some of them mentioned hereinbelow.

TABLE 4

Identities and concentrations of major compounds in turmeric oil 12B, fraction FI-2 and in sub-fractions FII-1 to FII-7 determined by GC/MS analysis

| # | RT (min) | Compound in fraction FII | Conc. in FII (%) | Conc. in 12B (%) | Concentration in sub-fractions (%) | | | | | | |
|---|---|---|---|---|---|---|---|---|---|---|---|
| | | | | | FII-1 | FII-2 | FII-3 | FII-4 | FII-5 | FII-6 | FII-7 |
| 1 | 19.70 | 1,3-diisopropyl-5-methylbenzene($C_{13}H_{20}$) | 2.4 | 0.14 | 4.7 | 0.11 | — | — | 13.8 | 8.0 | — |
| 2 | 20.33 | unidentified | 0.9 | 0.16 | 1.8 | — | — | — | 3.8 | 1.2 | — |
| 3 | 24.64 | ar-turmerol | 4.5 | 0.22 | — | — | 4.8 | 15.4 | 2.0 | — | — |
| 4 | 25.31 | Several - main: $C_{15}H_{24}O$ alcohol similar to spathulenol | 4.2 | several comp. | (a) | (a) | 13.8 | 8.7 | — | — | — |
| 5 | 25.45 | $C_{15}H_{26}O$ alcohol similar to trans-sesquisabinene hydrate | 3.1 | 0.17 | — | <2.4 (b) | 10.2 | — | — | — | — |
| 6 | 25.77 | $C_{15}H_{26}O$ alcohol - hinesol, agarospirol or valerianol | 3.0 | 0.17 | 2.1 | 9.9 | — | — | — | — | — |
| 7 | 25.86 | 2 compounds - main: similar to cis-sesquisabinene hydrate | 2.2 | 0.09 | — | — | — | — | 2.6 | — | — |
| 8 | 25.96 | $C_{15}H_{24}O$ alcohol - similar to β-biotol | 4.0 | <0.59 | (2.1) (d) | (0.9) (d) | (6.8) (c) | 17.4 | — | — | — |
| 9 | 26.60 | ar-turmerone | 1.7 | 12.7 | — | — | 1.1 | 0.13 | 2.9 | 1.4 | — |
| 10 | 26.73 | β-bisabolol | 3.7 | in a big peak | 10.0 | <0.56 (b) | <1.3 (b) | — | — | — | — |
| 11 | 27.14 | α-bisabolol | 1.2 | in a big peak | 0.5 | 5.7 | — | — | — | — | — |
| 12 | 27.18 | Probably $C_{14}H_{22}O$ ketone (e) | 0.85 | 0.065 | | 8.8 | | | | | |
| 13 | 27.38 | Two unidentified | 2.3 | in a big peak | 6.4 | 2.9 | 1.9 | 0.9 | — | — | — |
| 14 | 27.46 | Probably $C_{15}H_{20}O$ ketone (f) and traces of curlone | 2.4 | in a big peak | — | — | — | — | 8.8 | 5.0 | — |
| 15 | 28.22 | 6S,7R-bisabolone | 4.0 | 0.29 | 12.0 | 2.0 | 0.7 | — | — | — | — |
| 16 | 28.38 | α-oxobisabolene | 12.0 | 1.1 | 39.4 | 3.1 | 0.7 | — | 0.16 | — | — |
| 17 | 29.42 | $C_{15}H_{22}O$ ketone - similar to [E]-α-atlantone | 2.2 | 0.15 | 0.09 | — | 1.0 | — | — | 0.9 | 4.4 |
| 18 | 30.94 | $C_{15}H_{24}O$ ketone | 1.2 | 0.04 | — | — | — | — | — | — | 8.7 |

(a) Another compound
(b) In a mixture of compounds
(c) Another alcohol (similar to γ-eudesmol)
(d) Yet another alcohol (similar to α-acorenol)
(e) 4-[1,5-dimethyl-4-hexenyl]-2-cyclohexen-1-one, cas # 1723-80-4 (MW = 206).
(f) Like 3,3,4-trimethyl-4-[4-methylphenyl]cyclopentanone, cas # 056077-23-7 (MW = 216), or $C_{15}H_{22}O_2$ (MW = 234).

Fraction FIII consisted of the most polar compounds in 12B. These compounds could be revealed in a preliminary HPLC analysis, but could not be analyzed by GC/MS. The GC/MS TIC chromatogram of fraction FIII exhibited a total peaks area being less than 25% of other fractions (FIG. 3). Yet, this fraction did show traces of ar-turmerone and small amounts of at least 3 unidentified compounds which were also identified in fractions FI-2 and FII.

Repellency and penetration prevention: As shown in Table 5 below, Turmeric oil 12B applied at a concentration of 50 $\mu g/cm^2$ exhibited substantial insect repellency and penetration prevention activities. These activities further increased when turmeric oil 12B was applied at a concentration of 640 $\mu g/cm^2$.

ar-turmerone applied at different concentrations in a repellency bioassay resulted in increasing repellency activities as a function of concentration (FIG. 2). The effect of ar-turmerone concentration (Conc.) on insect repellency activity (%) was estimated as: % insect repellency=$100[1 -0.239/\text{Conc.}-\exp(-0.0286*(\text{Conc.})]$.

As is shown in Table 5 below, turmeric oil 12B applied at a concentration of 50 $\mu g/cm^2$ resulted in 60% repellency. Since ar-turmerone comprised only 13% of the turmeric oil content its effective concentration was equivalent to 6.5 $\mu g/cm^2$. In comparison, ar-turmerone required to achieve 60% repellency was estimated to be 32 $\mu g/cm^2$ (FIG. 2). Clearly, ar-turmerone could not be the sole substance responsible for the repellency capacity of turmeric oil 12B.

As is shown in Table 5 below, all four main fractions of turmeric oil 12B (FI-1, FI-2, FII and FIII) exhibited repellent activity, thus indicating that multiple compounds in turmeric oil 12B have insect repelling activity. Similarly, three main fractions of turmeric oil 12B (FI-1, FII and FIII) exhibited substantial penetration prevention activity, thus indicating that multiple compounds present in turmeric oil 12B have insect penetration prevention activity.

TABLE 5

Repellency and penetration prevention effects of ar-turmerone, turmeric USA essential oil 12B and its fractions

| Source of Material | Fraction | Non-choice test (%) (640 μg/cm$^2$) | Non-choice test (%) (50 μg/cm$^2$) | Choice Test (%) (50 μg/cm$^2$) | Repellency test (%) (50 μg/cm$^2$) | Repellency[1] | Penetration prevention effect[1] |
|---|---|---|---|---|---|---|---|
| USA essential oil 12B | | 90 | 12 | 80 | 60 | ++ | ++ |
| ar-turmerone | | na | −483 | 89 | 75 | +++ | 0 |
| Main fractionation | FI-1 | −36 | 36 | 40 | 34 | + | ++ |
| | FI-2 | 93 | −218 | 44 | 35 | + | 0 to + |
| | FII | 86 | −36 | 85 | 58 | ++ | ++ |
| | FIII | 30 | −9 | 88 | 43 | ++ | ++ |
| FII sub-fractionation | FII-1 | 29 | −164 | 78 | 56 | ++ | + |
| | FII-2 | −123 | 52 | 33 | 77 | +++ | +++ |
| | FII-3 | −70 | 13 | 68 | 68 | +++ | +++ |
| | FII-4 | 22 | 0 | 74 | −25 | 0 | ++ |
| | FII-5 | 89 | 48 | 63 | 35 | + | ++ |
| | FII-6 | 61 | 83 | 0 | −30 | 0 | +++ |
| | FII-7 | 58 | 0 | 66 | 7 | 0 | + |

[1]Repellency and penetration prevention effect at 50 μg/cm$^2$, expressed in 4 arbitrary classes: 0 (no effect), +, ++, +++ (strong effect).

Identity of biologically active turmeric sub fractions and compounds: As shown in Table 5 above, fraction FI-1 exhibited mild repellency activity. This was attributed to one or more terpenoids, namely ar-curcumene, α-zingiberene, β-bisabolene or β-sesquiphellandrene. The repellency activity of fraction FI-1 was equivalent to that of 15 μg/cm$^2$ ar-turmerone in repellency bioassay. Since the concentration of the 4 terpenoids was 28.5 μg/cm$^2$ in repellency bioassay (assuming equal contribution of each), the repellency efficiency of these compounds was assumed to be lower than that of ar-turmerone.

Fraction FI-2 also exhibited a mild repellency activity, which was attributed primarily to ar-turmerone (present in FI-2 at a concentration equivalent to 15 μg/cm$^2$ in the repellency bioassay). The repellency efficiency of other sesquiterpene ketones present in this fraction was substantially lower than that of ar-turmerone.

Fraction FII which comprised only 10% (w/w) of turmeric oil 12B, exhibited the strongest repellency activity, as compared with the other three main fractions.

Sub-fractions FII-2 and FII-3 exhibited the highest repellency activity, as compared with other FII sub-fractions. On the other hand, sub-fractions FII-2, FII-3 and FII-6 exhibited the highest penetration prevention activity.

The insect repellent and penetration prevention activities of fraction FII were mainly attributed to sesquiterpene alcohols including, for example, hinesol, agarospirol, valerianol, a $C_{15}H_{26}O$ alcohol similar to trans-sesquisabinene hydrate, a $C_{15}H_{26}O$ alcohol similar to cis-sesquisabinene hydrate, β-bisabolol, α-bisabolol, γ-eudesmol, a $C_{15}H_{26}O$ alcohol similar to α-acorenol, ar-turmerol, a $C_{15}H_{24}O$ alcohol similar to spathulenol, a $C_{15}H_{24}O$ alcohol similar to β-biotol, α-copaen-11-ol, [E]-nerolidol; grossonorol and tau-cadinol.

The overall repellency capacity of fraction FII was equivalent to 32 μg/cm$^2$ ar-turmerone in the repellency test, or to 64% ar-turmerone in fraction FII. On the other hand, the estimated concentration of all sesquiterpene alcohols in fraction FII could not exceed 20%. Thus, the repellency efficiency of the sesquiterpene alcohols of fraction FII is substantially higher (at least three fold) than the repellency efficiency of ar-turmerone.

Example 3

Biological Activities and GC/MS Analyses of Several Turmeric Essential Oils

Materials and Methods:

Turmeric essential oils: 12B, Cedar Vale, USA; 47, Sabinsa, India; 48, Exotic Naturals, India; 60, Henry Lamotte, Germany; 80, Galil Aroma, Israel; and 82, Galil Aroma, Israel.

Insects: As in Example 2 hereinabove.

Insect repellency, non-choice and choice bioassays: Bioassays were performed as described in Example 2 hereinabove.

GC/MS analysis: Analysis was performed as described in Example 2 above.

Results:

The insect repellency and penetration-prevention activities of several turmeric essential oil samples are shown in Table 6 below. All samples exhibited strong repellency capacity. GC/MS analyses of the turmeric essential oil samples are shown in Table 7 below.

TABLE 6

Comparative insect repellency and penetration prevention activities of several turmeric essential oils

| In house code | Source of oil[4] | Repellency test[1] (%) | Choice test[1] (%) | Non-choice test[2] (%) |
|---|---|---|---|---|
| 12B | Cedar Vale - USA | 60 | 80 | 90 |
| 47 | Sabinsa - India | 88 | 86 | −126 |
| 48 | Exotic Naturals - India | 74 | | −54 |
| 60 | Henry Lamotte - Germany Oleoresin[3] | 80 | | 54 |
| 80 | Galil Aroma - Israel Oleoresin[3] (8.5% curcuminoids) | 74 | 63 | 38 |
| 82 | Galil Aroma - Israel Oleoresin[3] (32% curcuminoids) | 74 | 72 | 46 |

[1]Tested at 50 μg/cm$^2$.
[2]Tested at 640 μg/cm$^2$.
[3]Purchased oleoresin extracted with petroleum ether (b.p. 40-60° C.).
[4]Source of turmeric plant: India for # 12B, 47, 48 and 60; Far east for # 80; Ethiopia for # 82.

TABLE 7

Comparative composition (main and other interesting compounds)
of several turmeric essential oils, analyzed by GC/MS

| # | Compound | Component concentration (%) in essential oils (of Table 6) | | | | | |
|---|---|---|---|---|---|---|---|
| | | 12B | 47 | 48 | 60 | 80 | 82 |
| 1 | α-phellandrene | 2.80 | 0.10 | 4.20 | <0.01 | <0.01 | <0.01 |
| 2 | p-cymene | 0.74 | 0.06 | 1.90 | <0.01 | <0.01 | <0.01 |
| 3 | eucalyptol | 0.98 | 0.14 | 1.70 | 0.01 | <0.01 | 0.02 |
| 4 | ar-curcumene | 2.00 | 2.40 | 5.10 | 2.30 | 2.30 | 1.60 |
| 5 | α-zingiberene | 8.10 | 3.10 | 3.60 | 3.40 | 1.90 | 3.20 |
| 6 | β-bisabolene | 1.10 | 0.54 | 0.95 | 0.56 | 0.53 | 0.46 |
| 7 | β-sesquiphellandrene | 7.10 | 2.40 | 3.70 | 3.10 | 3.20 | 2.40 |
| 8 | ar-turmerone | 12.70 | 27.0[1] | 28.30 | 33.9[1] | 35.30 | 24.9[1] |
| 9 | turmerone | 29.60 | 24.1[1] | 15.60 | 18.7[1] | 18.10 | 28.1[1] |
| 10 | curlone | 12.90 | 16.50 | 11.30 | 16.40 | 19.20 | 19.50 |
| 11 | [E]-α-atlantone | 2.00 | 3.50 | 1.80 | 2.80 | 3.40 | 3.40 |
| 12 | α-bisabolone | 1.10 | 1.10 | 0.65 | 1.10 | 1.10 | 0.76 |
| 13 | ar-turmerol | 0.22 | 0.69 | 0.89 | 0.87 | 0.50 | 0.69 |

[1]The peaks of ar-turmerone and turmerone are not well separated in the TIC chromatogram - therefore, approximate concentration (the total concentration of both compounds is correct).

The results indicate that (i) major quantitative differences exist in primary and secondary component concentrations in turmeric essential oil samples obtained from different sources; (ii) main monoterpenes (compounds 1-3), main sesquiterpenes (compounds 4-7) and sesquiterpene ketones other than ar-turmerone (compounds 8-12) in turmeric essential oils are ineffective as insect repellants or antifeedants; and (iii) sesquiterpene alcohols contributed substantially to the overall repellency capacity of the essential oils.

Example 4

Insect Repellency and Penetration Prevention Efficacy of "Turmeric Oleoresin Solid Residue"

Materials and Methods

Turmeric oleoresin solid residue: Turmeric oleoresins were purchased from Henry Lammote GmbH (Germany) and Galil Aroma (Israel). The turmeric oleoresin samples were extracted 3 to 4 times with petroleum ether (b.p. 40-60° C.), or with diethyl ether. Following removal of the liquid extract, the remaining deposit was rinsed several times with the solvent and the leftover solvent was then removed by evaporation in an open hood. The remaining fraction of turmeric oleoresin was considered as the solid residue of the turmeric oleoresin.

Insects: As in Example 2 above.

Insect repellency, non-choice and choice bioassays: Bioassays were performed as described in Example 2 hereinabove.

Results

The biological activity of turmeric oleoresin solid residue (TOSR) differed dramatically among different samples. As shown in Table 8 below, TOSR of plants originated from the Far East exhibited strong penetration prevention. TOSR of plants originated from Ethiopia exhibited strong penetration prevention as well as repellency activities. On the other hand, TOSR of plants originated from India exhibited very little repellency or penetration prevention activity.

TOSR generated followed extraction with the polar solvent diethyl ether exhibited the same penetration prevention capacity, as compared with TOSR generated followed extraction with the non-polar solvent petroleum ether (Table 8). It is expected that the TOSR is composed of relatively nonvolatile polar compounds which are not soluble even in diethyl ether.

TABLE 8

Comparative insect repellency and penetration prevention
activities of several turmeric oleoresin solid residues[1]

| In house code | Source of turmeric oleoresin[3] | Oleoresin extraction solvent | Repellency test[2] (%) | Choice test[2] (%) | Non-choice test[2] (%) | Repellency[7] | Antifeedant effect[7] |
|---|---|---|---|---|---|---|---|
| 65 | Henry Lamotte - Germany | Petroleum ether | | -8 (50) | 50 (50) 0 (640) | 0 | + |
| 95 | Henry Lamotte - Germany[6] | Petroleum ether | | -200 (50) | 25 (640) | 0 | + |
| 81 | Galil Aroma - Israel Oleoresin (8.5% curcuminoids) | Petroleum ether | 28 (100)[4] | 100 (50) 63 (100) | 77 (640) | + | +++ |
| 83 | Galil Aroma - Israel Oleoresin (32% curcuminoids) | Petroleum ether | 72 (50) 40 (100)[4] | 63 (50) 100 (100) | 70 (36) 62 (50) 59 (640) | ++ to +++ | +++ |
| 84 | Galil Aroma - | Diethyl ether | | | 43 (640) | na | ++ to +++ |

TABLE 8-continued

Comparative insect repellency and penetration prevention
activities of several turmeric oleoresin solid residues[1]

| In house code | Source of turmeric oleoresin[3] | Oleoresin extraction solvent | Repellency test[2] (%) | Choice test[2] (%) | Non-choice test[2] (%) | Repellency[7] | Anti-feedant effect[7] |
|---|---|---|---|---|---|---|---|
| 86 | Israel Oleoresin (32% curcuminoids) | | | | 55 (640)[5] | | |

[1] The fraction of oleoresin that remains after the removal of the essential oil from it.
[2] The tested concentration in μg/cm² is given in parenthesis.
[3] Source of turmeric plant: India for # 65, 95; Far east for # 81; Ethiopia for # 83, 84, 86.
[4] Test results after a week (instead of 24 hours).
[5] Results for two extracted samples.
[6] Another lot.
[7] Repellency and penetration prevention effect at 50 μg/cm², expressed in 4 arbitrary classes: 0 (no effect), +, ++, +++ (strong effect).

Example 5

Turmeric Extracts Impregnation in Packaging Materials

Turmeric USA essential oil 12A was successfully embedded in a commercial PVC sheet, either 0.83 or 0.10 mm thick. The turmeric extract did not affect the physical appearance of the polyvinyl chloride (PVC) and bioassays performed on the turmeric treated PVC resulted in substantial insect penetration-prevention efficiency (data not shown). In addition, turmeric extracts were dissolved in PSA lacquer at 1:4 ratio and then brushed over bags and boxes of breakfast cereal. Bioassays performed on the turmeric treated packages resulted in substantially improved insect penetration-prevention efficiency (data not shown). In another experiment, turmeric oil extract was successfully dissolved in the lacquer and glue being used in industrial manufacturing of a packaging film. The turmeric-amended lacquer remained smooth and well spread over the sheets and the turmeric-amended glue dried properly.

Hence, turmeric extracts can be effectively impregnated in various conventional packaging materials without affecting their physical quality while conferring pest resistance.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

Ahmed, S. M. and Ahamad, A. (1992) Efficacy of some indigenous plants as pulse protectants against *Callosobruchus chinensis*. International Pest Control, 1992 (2): 54-56.

Anonymous (1989). JMP User's Guide. First Printing. SAS Institute Inc. pp. 464, Cary N.C., USA.

Anonymous (1992). *Neem: A Tree for Solving Global Problems*. National Academy Press, National Research Council, pp. 141, Washington, D.C.

Aratanechemuge, Y., Komiya, T., Moteki, H., Katsuzaki, H., Imai, K. and H. Hibasami (2002) Selective induction of apoptosis by ar-turmerone isolated from turmeric (*Curcuma longa* L) in two human leukemia cell lines, but not in human stomach cancer cell line. International Journal of Molecular Medicine 9:481-484. 48

Golding, B. T. and E. Pombo-Villar (1992) Structures of α- and β-Turmerone. Journal of Chemical Society Perkin Transactions 1:1519-1524.

Golob, P., Moss, C., Dales, M., Fidgen, A., Evans, J. and I. Gudrups (1999) The Use Of Spices And Medicinals As Bioactive Protectants For Grains. FAO Agricultural Services Bulletin No. 137. Food and Agriculture Organization of the United Nations Rome.

He, X., Lin, L., Lian, L. and M. Lindenmaier (1998) Liquid chromatography-electrospray mas spectrometric analysis of curcuminoids and sesquiterpenoids in turmeric (*Curcuma longa*). Journal of Chromatography A, 818:127-132.

Highland, H. A. (1977). Chemical treatments and construction features used for insect resistance. *Package Development and Systems* 13(3)251-256.

Islam, B. N. (1987) Use of some extracts from Meliaceae and Annonaceae for control of rice hispa, *Dicladispa armigera* and the pulse beetle *Callosobruchus chinensis*.

Schmutterer, H. and Asher K. R. S., eds. *Proceedings of the Third International Neem Conference*, p. 217-242. July 1986, Nairobi, Kenya.

Isman, M. B., Koul, 0., Luczynski, A. and Kaminski, J. (1990). Insecticidal and Antifeedant Bioactivities of Neem Oils and Their Relationship to Azadirachtin Content. *Journal of Agricultural Food and Chemistry* 38, 1406-1411.

Jilani, G. and Su, H. C. F. (1983). Laboratory studies on several plant materials as insect repellents for protection of cereal grains. *Journal of Economic Entomology* 76, 154-157.

Jilani, G. and Saxena, R. C. (1990). Repellent and Feeding Deterrent Effects of Turmeric Oil, Sweetflag Oil, Neem Oil, and a Neem-Based Insecticide Against Lesser Grain Borer (Coleoptera: Bostrychidae). *Journal of Economic Entomology* 83, 629-634.

Jilani, G., Saxena, R. C. And Rueda, B. P. (1988) Repellent and growth-inhibiting effects of Turmeric oil, Sweet flag oil, Neem oil, and "Margosan-O" on red flour beetle (Coleoptera: Tenebrionidae). *J. Economic Entomology,* 81(4): 1226-1230.

Jilani, G., Saxena, R. C., and Reuda, B. P. (1988). Repellent and growth-inhibiting effects of turmeric oil, sweetflag oil, neem oil, and Margosan-O on red flour beetle (Coleoptera: Tenebrionidae). *Journal of Economic Entomology* 81, 1226-1230.

Jotwani, M. G. and Srivastava, K. P. (1984). A review of neem research in India in relation to insects. In *Proceedings of the 3th International Neem Conferance.* eds H. Schmutterer and K. R. S. Ascher, pp. 43-56. Eschborn, Germany, 1983.

Koul, O. (1992). Neem allelochemicals and insect control. In *Allelopathy, basic and Applied Aspects* ed. by S. J. H. Riavi and V. Riavi, pp. 389-412. Chapman&Hall, London, 1992.

Laudani, H., Davis, D. F. and Swank, G. R. (1955). A laboratory method of evaluating the repellency of treated paper to stored-product insects. *Technical Association of the Pulp and Paper Industry* 38, 336-341.

Leal, P. F., Braga, M. E. M., Sato, D. N., Carvalho, J. E., Marques, M. O. M. and Meireles, M. A. A (2003). Functional properties of spice extracts obtained via supercritical fluid extraction. *J. Agri. Food Chem.* 51, 2520-2525.

Lee, H., Shin, et al., (2001) Insecticidal activities of ar-turmerone identified in *Curcuma longa* rhizome against *Nilaparvata lugens* (Homoptera; Delphacidae) and *Plutella xylostella* (Lepidoptera; Yponomeutidae). Journal of Asia Pacific Entomology 4(2):181-185.

Malik, M. M. and Naqvi, S. H. M. (1984). Screening of some indigenous plants as repellents or antifeedants for stored grain insects. *Journal of Stored Products Research* 20, 41-44.

Martins, A. P., Salgueiro, M., Gonsalves, M. J., Proneça da Cunha, A., Vila, R., Cañigueral, S., Mazzoni, V., Tomi, F. and Casanova, J (2001) Essential oil composition and antimicrobial activity of three Zingiberaceae from S. Tomé e Principe. *Planta Med* 67, 580-584.

McDonald, L. L., Guy, R.H. and Spiers, R. D. (1970). Preliminary evaluation of new candidate materials as toxicants, repellents, and attractants against stored-product insects. *USDA Mktg Res. rep.* 882, 8 pp.

Navarro, S. Ferizli, A. H. and R. Dias (1998) Insect Repelling Food Packaging Materials. Israel Pat. No. 125,130 and Australia Patent No. 4,530,499.

Navarro, S., Ferizli, A. G., Dias, R., and Rinder, M. (1998). A device for testing resistance of packaging films to penetration by storage insects. (unpublished internal report at the ARO).

Ohshiro M., Kuriyonagi, M. and A. Ueno (1990) Structures of sesquiterpenes from *Curcuma longa.* Phytochemistry, 29(7):2201-2205.

Perry, L. M. (1980) *Medicinal plants of East and Southeast Asia.* Massachusetts Institute of Technology, USA.

Pranata, R. I. (1984) Possibility of using Turmeric (*Curcuma longa* L.) for controlling storage insects. *Biotrop Newsletter,* 45:3.

Raina, V. K., S. K. Srivastava, et al. (2002) Essential oil composition of *Curcuma longa L. cv. Roma from the plains of northern India. Flavour and Fragrance Journal* 17(2): 99-102.

Schmutterer, H. (1988). Potential of azadirachtin-containing pesticides for integrated pest control in developing and industrialized countries. *Journal of Insect Physiology* 34, 713-719.

Su, H. C. F., Horvay, R. and Jilani, G. (1982). Isolation, purification, and characterization of insect repellents from *Curcuma longa* L. *Journal of Agricultural Food and Chemistry* 30, 290-292.

Subramanyam, B. and D. W. Hagstrum. (1996) Resistance Measurement and Management. In Integrated Management of Insects in Stored Products ed. by Subramanyam B. and Hagstrum D. W. pp. 331-397. Marcel Dekker, Inc. New York Zwavig, J. H. and R. Boss (1992) Analysis of the essential oils of five *Curcuma* species. Flavour and Fragrance Journal 7(1):19-22.

What is claimed is:

1. A pest control composition comprising at least 10% by weight of at least one sesquiterpene alcohol, and further comprising at least 10% by weight of a turmeric oleoresin solid residue, the composition being identified for use in controlling pest infestation, wherein said pest is an insect.

2. The pest control composition of claim 1, wherein said sesquiterpene alcohol is selected from the group consisting of hinesol, agarospirol, valerianol, β-bisabolol, α-bisabolol, γ-eudesmol, ar-turmerol, α-copaen-11-ol, [E] -nerolidol and gossonorol, and any combination thereof.

3. The pest control composition of claim 1, comprising at least 10% by weight of at least one sesquiterpene alcohol, at least 10% by weight of a turmeric oleoresin solid residue and ar-turmerone.

4. The pest control composition of claim 3, wherein concentrations of said sesquiterpene alcohol, said turmeric oleoresin solid residue and said ar-turmerone are selected such that the composition exhibits insect repellant and antifeedant activities.

5. A method of controlling pest infestation, comprising exposing the pest to the composition of claim 1, thereby controlling pest infestation.

6. The method of claim 5, wherein said sesquiterpene alcohol is selected from the group consisting of hinesol, agarospirol, valerianol, β-bisabolol, α-bisabolol, γ-eudesmol, ar-turmerol, α-copaen-11-ol, [E]-nerolidol and gossonorol, and any combination thereof.

7. The method of claim 5, wherein said exposing is effected by a method selected from the group consisting of spraying, soaking, dipping, drenching, mixing, impregnating, fumigating, fogging, coating and dusting.

* * * * *